(12) United States Patent
Wu et al.

(10) Patent No.: US 10,582,836 B1
(45) Date of Patent: Mar. 10, 2020

(54) SYSTEM AND METHOD OF LARYNGOSCOPY SURGERY AND IMAGING

(71) Applicant: The Trustees of Dartmouth College, Hanover, NH (US)

(72) Inventors: Xiaotian Wu, East Greenwich, RI (US); Joseph A. Paydarfar, Hanover, NH (US); Ryan J. Halter, Orford, NH (US)

(73) Assignee: The Trustees of Dartmouth College and Dartmouth-Hitchcock Clinic

( * ) Notice: Subject to any disclaimer, the term of this patent is extended or adjusted under 35 U.S.C. 154(b) by 0 days.

(21) Appl. No.: 15/920,395

(22) Filed: Mar. 13, 2018

Related U.S. Application Data

(60) Provisional application No. 62/470,846, filed on Mar. 13, 2017.

(51) Int. Cl.
| | |
|---|---|
| *A61B 1/00* | (2006.01) |
| *A61B 1/06* | (2006.01) |
| *A61B 1/267* | (2006.01) |
| *A61B 1/05* | (2006.01) |

(52) U.S. Cl.
CPC ........ *A61B 1/00149* (2013.01); *A61B 1/0669* (2013.01); *A61B 1/267* (2013.01); *A61B 1/00142* (2013.01); *A61B 1/05* (2013.01)

(58) Field of Classification Search
CPC . A61B 1/00149; A61B 1/0669; A61B 1/1267; A61B 1/00142; A61B 1/05
USPC ....... 600/185, 193, 196, 227, 228, 229, 230, 600/231, 232, 233
See application file for complete search history.

(56) References Cited

U.S. PATENT DOCUMENTS

| | | | | |
|---|---|---|---|---|
| 4,884,558 A | | 12/1989 | Gorski et al. | |
| 5,888,190 A | * | 3/1999 | Meyer ................ | F16M 11/041 248/278.1 |
| 6,904,630 B2 | * | 6/2005 | Al-Kassim .......... | A61B 6/0442 378/209 |
| 8,529,442 B2 | * | 9/2013 | Pacey .................. | A61B 1/267 600/187 |
| 2004/0172012 A1 | * | 9/2004 | Otsuka ................ | A61B 90/50 606/1 |
| 2006/0063973 A1 | * | 3/2006 | Makower ........... | A61B 1/00135 600/114 |
| 2007/0055103 A1 | * | 3/2007 | Hoefig ............... | A61B 1/00179 600/173 |
| 2008/0091066 A1 | * | 4/2008 | Sholev ............... | A61B 1/00016 600/112 |
| 2008/0177285 A1 | * | 7/2008 | Brock ................ | A61B 17/0469 606/130 |
| 2009/0264708 A1 | * | 10/2009 | Pacey .................. | A61B 1/267 600/187 |

(Continued)

*Primary Examiner* — Pedro Philogene
*Assistant Examiner* — David C Comstock
(74) *Attorney, Agent, or Firm* — Loginov & Associates, PLLC; William A. Loginov

(57) ABSTRACT

A support rig for a medical instrument can hold a medical instrument that is inserted into a patient in a fixed position and orientation relative to patient, so that the position and orientation of the medical instrument is not affected by the breathing or other motion of the patient. The support rig and medical instrument can non-metallic, so that an image can be taken of the patient while the medical instrument is inserted in the patent and held by the support rig.

16 Claims, 26 Drawing Sheets

(56) References Cited

U.S. PATENT DOCUMENTS

2018/0014851 A1* 1/2018 Hansen .................... A61B 1/05
2018/0200013 A1* 7/2018 Elhawary ............... A61B 34/30

* cited by examiner

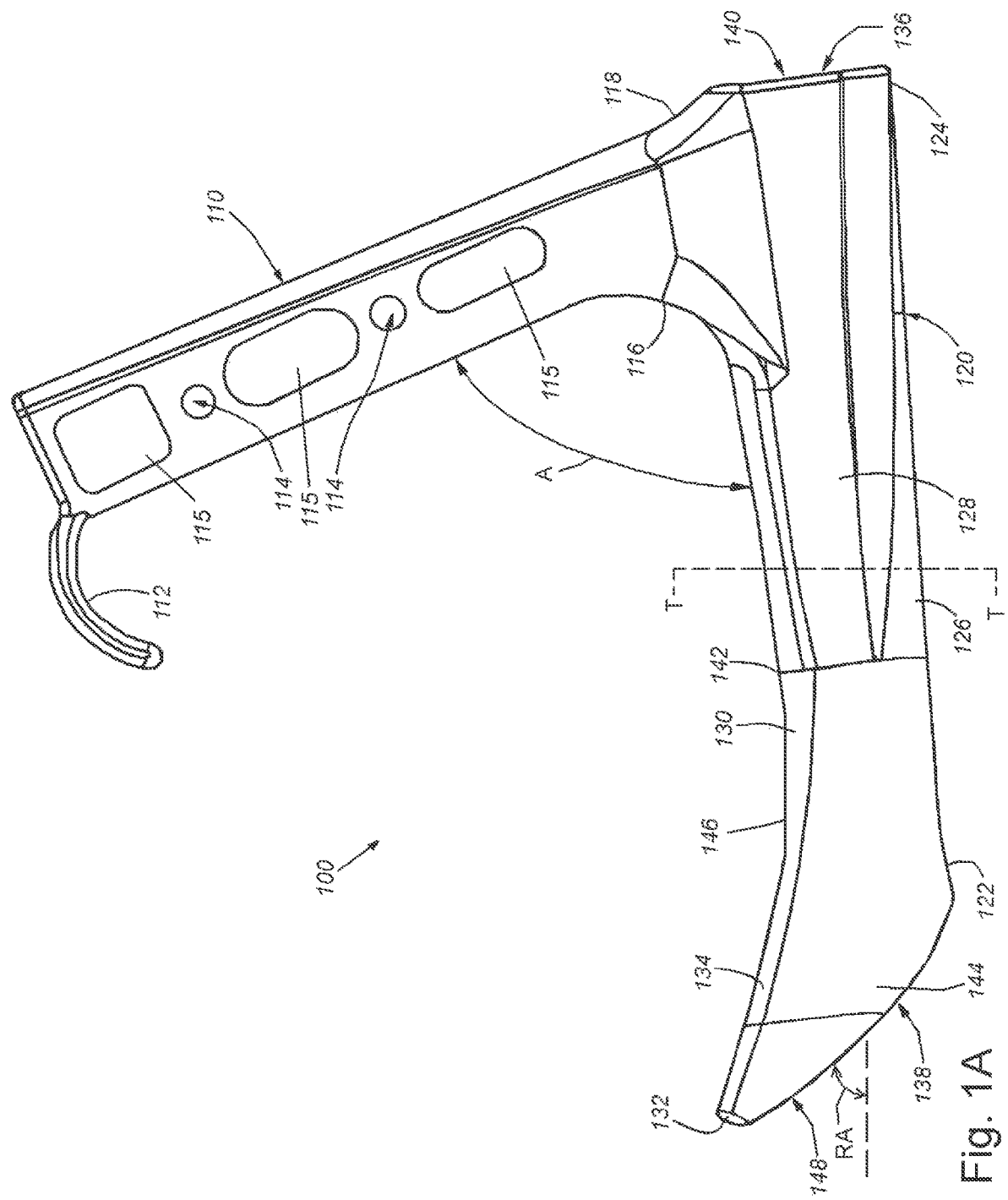

SYSTEM AND METHOD OF LARYNGOSCOPY SURGERY AND IMAGING

RELATED APPLICATION

This application claims the benefit of U.S. Provisional Application Ser. No. 62/470,846, filed Mar. 13, 2017, entitled SYSTEM AND METHOD OF LARYNGOSCOPY SURGERY AND IMAGING, the entire disclosure of which is herein incorporated by reference.

STATEMENT REGARDING FEDERALLY SPONSORED RESEARCH OR DEVELOPMENT

This invention was made with government support under Grant # TR001086 awarded by the National Institutes of Health. The government has certain rights in the invention.

FIELD OF THE INVENTION

This invention relates to a system and method for using a medical instrument.

BACKGROUND OF THE INVENTION

Laryngoscopy is an endoscopy of the larynx, a part of the throat. A laryngoscope is a hand held medical instrument used for visual examination of the larynx and trachea of a patient during a laryngoscopy. It is a medical procedure that is used to obtain a view, for example, of the vocal folds and the glottis. The instrument appears in two basic forms, an indirect laryngoscope and a direct laryngoscope. The indirect form utilizes a mirror held near the back of the pharynx while a light is directed upon it from a reflector worn on the forehead of the examiner. This is usually performed in the office setting. The second type, a direct laryngoscope, is equipped with a built in illuminating device and a blade. Direct laryngoscopy may be performed to facilitate tracheal intubation during general anaesthesia or cardiopulmonary resuscitation or for surgical procedures on the larynx or other parts of the upper tracheobronchial tree. Direct laryngoscopy is carried out (usually) with the patient lying on his or her back; the laryngoscope is inserted into the mouth and the tongue is moved out of the line of sight. Depending on the type of blade (a projecting structure of the laryngoscope to move the epiglottis and tongue forward to provide an unobstructed view of the larynx and trachea) used, the laryngoscope is inserted either anterior or posterior to the epiglottis and then lifted with an upwards and forward motion ("away from you and towards the roof of the mouth"). This move makes a view of the glottis possible. This procedure can be done in an operation theatre with full preparation for resuscitative measures to deal with respiratory distress. Video laryngoscopes are currently available, and they employ a variety of features such as a monitor on the handle and or channels to assist in guiding the endotracheal tube into the trachea.

Intraoperative CT (computed tomography) and MR (magnetic resonance) imaging affords the opportunity to study the soft tissue deformation that occurs as a result of instrumentation of the upper aerodigestive tract during operative laryngoscopy and other trans-oral surgical procedures. Transoral surgery (TOS) has revolutionized management of tumors of the pharynx and larynx. Intraoperative surgical navigation may play a role in assessing tumor extent and avoidance of critical structures in TOS but has not been studied. Unlike the case with imaging acquired for sinus and skull base surgery, the upper aerodigestive tract anatomy changes once the patient undergoes general anesthesia and during suspension laryngoscopy, thus rendering preoperative imaging unusable. A better understanding of how the upper aerodigestive tract deforms during instrumentation is critical in areas such as airway management during intubation and trans-oral resection of benign and malignant tumors of the upper aerodigestive tract. Intraoperative imaging such as CT or MRI would allow for improved visualization and understanding of this upper aerodigestive tract deformation. However, intraoperative images acquired during surgery of the upper aerodigestive tract can be partially obscured by images and reflections of the laryngoscope itself (called "artifacts") because the TOS instrumentation, including laryngoscopy devices and other surgical retractors, is made of stainless steel and is contraindicated in MR and CT imaging. This is distinct disadvantage of the conventional metal laryngoscopes. A further disadvantage is that conventional laryngoscopes are mounted on the thorax of the patient, such that the respiration of that individual can cause the laryngoscope to rise and fall, creating motion-induced distortions and inaccuracies in the imaging itself.

It would be desirable to have a laryngoscope that is compatible with these imaging systems, does not rest on the patient's body, and to provide a device that is potentially customized to the anatomical specificities of an individual patient's anatomy.

SUMMARY OF THE INVENTION

The present invention overcomes the disadvantages of the prior art by providing a system and method for using a medical instrument, such as a laryngoscope, and for holding the medical instrument in a fixed position and orientation relative to the patient after the medical instrument has been inserted into the patient. The present invention further overcomes the disadvantages of the prior art by enabling a user to obtain an MR image or CT scan of at least a portion of a patient while the medical instrument remains inserted in the patient and held in a support rig that can hold the medical instrument in a fixed position and orientation relative to the patient.

In an embodiment, a positioning device for a medical instrument can include an adjuster that can include a worm gear, an axle, and a medical instrument holder. The medical instrument holder can include an engagement arm adapted to hold a medical instrument, an upper arc that can be a segment of a cylinder, wherein a central axis of the cylinder passes through a center of the axle, and a rack gear, wherein the rack gear is arranged on the upper arc, and an outer shell, wherein the axle can be engaged with the outer shell, and wherein the outer shell can hold the worm gear and the rack in engagement with each other, whereby the medical instrument holder can pivot around the central axis when the worm gear is turned. The positioning device can have a bore through the positioning device from a distal end to a proximal end. The bore can be through the adjuster. The positioning device can be made of at least one non-metallic material. The at least one non-metallic material can be poly(methyl methacrylate) (acrylic), or can be polyethylene, polycarbonate, polyamide (nylon), and/or polyvinyl chloride. The engagement arm can define a channel adapted to receive a medical instrument.

In an embodiment, a support apparatus for a medical instrument can include a tower, an arm hingedly mounted to the tower, and a positioning device for a medical instrument, wherein the positioning device can be adapted to be engaged with the arm. The positioning device can include an adjuster that can include a worm gear, an axle, and a medical instrument holder. The medical instrument holder can include an engagement arm adapted to hold a medical instrument, an upper arc that can be a segment of a cylinder, wherein a central axis of the cylinder passes through a center of the axle, and a rack gear, wherein the rack gear is arranged on the upper arc, and an outer shell, wherein the axle can be engaged with the outer shell, and wherein the outer shell can hold the worm gear and the rack in engagement with each other, whereby the medical instrument holder can pivot around the central axis when the worm gear is turned. The positioning device can be selectively engageable with the arm. The positioning device can be slidably engageable with the arm. The positioning device can have a bore through the positioning device, the bore adapted to have the arm inserted into the bore. The support apparatus can be made of at least one non-metallic material. The at least one non-metallic material can be poly(methyl methacrylate) (acrylic), or can be polyethylene, polycarbonate, polyamide (nylon), and/or polyvinyl chloride. The support apparatus can have a platform, wherein the tower extends upwardly from the platform. The tower can be releasably engageable with the platform, so that the tower can be removed from the platform before a patient is placed on the platform, and the tower can be engaged with the platform after the patient is placed on the platform. The tower can be hingedly engaged with the platform, so that the tower can be pivoted from a first position to a second position before a patient is placed on the platform, and the tower can pivoted from the second position to the first position after the patient is placed on the platform. The tower can be swivellingly engaged with the platform, so that the tower can be swiveled from a first position to a second position before a patient is placed on the platform, and the tower can swiveled from the second position to the first position after the patient is placed on the platform.

A method of using a laryngoscope support apparatus can include inserting a laryngoscope into the throat of a patient, engaging the laryngoscope with a support rig, wherein the support rig has a tower, an arm, and a positioning device, wherein the laryngoscope is engaged with the positioning device and is held in a fixed position and orientation relative to the patient, and wherein the support rig is non-metallic, and obtaining an image of the patient while the laryngoscope is inserted in the patient and the laryngoscope is engaged with the support rig, wherein the imaging is selected from the group consisting of CT scan, magnetic resonance imaging (MM), proton beam imaging, PET scan, X-ray, and electromagnetic tracking. The method can include performing a medical procedure on the patient.

BRIEF DESCRIPTION OF THE DRAWINGS

The invention description below refers to the accompanying drawings, of which:

FIG. 1A is a side view of a laryngoscope, according to an embodiment;

DETAILED DESCRIPTION

Figure 1B:
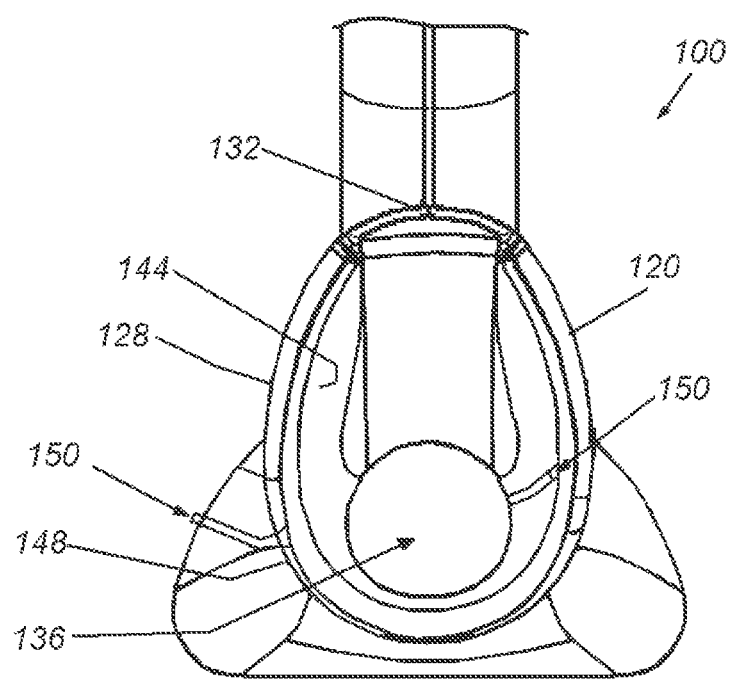
FIG. 1B is an end view of a distal end of an insertion member of a laryngoscope, according to an embodiment.

FIG. 1A is a side view of a laryngoscope, according to an embodiment. A laryngoscope 100 can be used to provide a user with a view of various structures inside of a patient's throat, including the glottis, vocal cords, larynx, and others. As used herein, a user can be a doctor, a surgeon, a radiologist, an anesthesiologist or other medical provider, and/or a hospital, a medical school, or other medical service providing organization. In an embodiment, a laryngoscope 100 can have a handle 110 and an insertion member 120. The handle 110 and the insertion member 120 can be at an angle that can be in a range of approximately 60-80 degrees. As shown in FIG. 1A, the insertion member and handle are at an angle A of approximately 72 degrees. The insertion member 120 can have a distal end 122 that is the end away from the handle that can be inserted into the mouth of a patient and the insertion member can have a proximal end 124 that is nearest to the handle.

The handle can have a hook 112, at least one securing hole 114, at least one weight-reducing hole 115, a distal fillet 116, and a proximal fillet 118. The at least one securing hole 114 can be used in securing the laryngoscope to a rig, explained more fully below. The at least one weight-reducing hole 115 can reduce the weight of the laryngoscope, while also reducing the cost of the material used in the laryngoscope and reducing the time required to produce the laryngoscope. A distal fillet 116 can be a curved member between the handle 110 and the insertion member 120. A polymer laryngoscope may have reduced material strength compared to a traditional metal laryngoscope. The distal fillet 116 can add strength to the laryngoscope by making the union between the handle 110 and the insertion member 120 free of corners or sharp angles, and by adding additional material between the handle 110 and the insertion member 120. A proximal fillet 118 can be a curved member between the handle 110 and the insertion member 120. The distal fillet 118 can add strength to the laryngoscope by making the union between the handle 110 and the insertion member 120 free of corners or sharp angles, and by adding additional material between the handle 110 and the insertion member 120. The distal fillet 116 and proximal fillet 118 can provide increased strength to the laryngoscope 100 at the union between the handle 110 and insertion member 120, so that the laryngoscope can withstand the forces imparted by the patient, while allowing the laryngoscope 100 to be made from a lightweight, non-metallic material that can be radiolucent.

In various embodiments, an insertion member 120 can include a tube 126. A tube 126 can be formed by at least one sidewall 128. The at least one sidewall 128 can be entirely enclosing so that when the insertion member 120 is viewed in cross-section along line T-T, the insertion member 120 can be in the shape of a circle, or the letter "D", or other closed conformations. The at least one sidewall 128 can be partially enclosing, so that when the insertion member 120 is viewed in cross section along line T-T, the at insertion member 120 can be in the shape of the letter "C", or an upside-down letter "L", or other open conformations. The insertion member 120 can have a blade 130. The blade 130 can have a leading edge 132. The leading edge 132 can be the most distal portion of the insertion member 120. A blade 130 can have a ramp 134 in a distal area of the blade. The ramp 134 can be an inclined area of the blade 130. The ramp 134 can be curved and/or angled upwards. The insertion member 120 can have a rib 146 that can extend along an upper portion of the insertion member. The rib 146 can be a region of thicker material that can add strength to the insertion member 120, so that the laryngoscope can withstand the forces imparted by the patient, while allowing the laryngoscope 100 to be made from a lightweight, non-metallic material that can be radiolucent. The rib 146 can be along the exterior of the insertion member 120, so that the increased material thickness does not obstruct the user's view through the laryngoscope. The rib 146 can be the region of the insertion member having the thickest material. The rib 146 can extend at least partially between the distal fillet 116 and the ramp 134. The rib 146 can extend entirely between the distal fillet 116 and the ramp 134.

The insertion member can have a neck 142 that can be an area of the insertion member between the distal end 122 and proximal end 124. The neck can be narrower than the distal 122 end and/or the proximal end 124. The insertion member 120 can have a bell 144 at the distal end 122. The bell 144 can be a taller and/or wider portion of the insertion member 120, so that the distal end can be larger than the neck 142. The ramp 134 can form part of the bell 144, so that the bell 144 can be taller than the neck 142. The bell 144 can have a rim 148 that can be the distal edge of the bell 144. The leading edge 132 can be raised up and away from the neck 142, and the leading edge 132 can form a portion of the rim 148. The rim 148 can be approximately two-dimensional and can be in a plane that is at an angle to the central lumen 136. The shape of the rim 148 can be approximately defined as a cylindric section that can be an intersection of a plane with a cylinder, with the plane at an angle approximately 45-65 degrees from the central axis of the cylinder. The rim 148 can be at a rim angle RA of approximately 45-65 degrees from the central axis of the insertion member. The rim 148 can be approximately the shape of a cylindric section having a portion of the cylindric section removed at the leading edge 132, so that the rim 148 can have a flattened area at the most distal portion of the insertion member where the ramp 134 meets the bell 144. When viewed from the side, the rim 148 can be in the shape of a portion of a parabola, with the angle of the rim increasing from the bottom of the rim to the leading edge. A rim with a parabolic shape can have an angle of approximately 20 degrees near the bottom of the rim, and the angle of the rim can approach approximately 65 degrees near the leading edge 132. The rim 148 can be continuously curved from one side of the leading edge 132 to the other side of the leading edge 132. The shape of the rim 148 can provide increased strength to the distal end of the insertion member, so that the insertion member can withstand the forces imparted by the patient's tough and throat, while allowing the insertion member to be made from a lightweight, non-metallic material that can be radiolucent.

The blade 130 can form the top of the tube 120. The tube 120 can have a central lumen 136. Central lumen 136 can be a passage through the insertion member 120. The central lumen 136 can have a distal orifice 138 that can be an opening at the distal end 122 of the insertion member 120. The central lumen 136 can have a proximal orifice 140 that can be an opening at the proximal end 124 of the insertion member 120. In alternate embodiments, the insertion member 120 can have a blade 130 without a tube 120. In alternate embodiments, the insertion member 120 can have a blade 130 without a sidewall 128.

FIG. 1B is an end view of the distal end an insertion member of a laryngoscope, according to an embodiment. In various embodiments, an insertion member can include at least one channel 150 adapted for introducing an additional instrument, such as a fiber optic camera, a suction tube or channel, tissue graspers and retractors, a laser fiber, or other tool or device used by a surgeon. The at least one channel 150 can extend at least partially from a distal end 122 to a proximal end 124 of the insertion member. The at least one channel can extend fully from a distal end 122 to a proximal end 124 of the insertion member. The at least one channel can be an enclosed conduit, a partially enclosed trough, a series of guides, or other means for holding an instrument. The at least one channel can be along an interior of a sidewall 128, along exterior of a sidewall 128, and/or housed within the sidewall 128. The rim 148 at the distal end of the bell 144 can be approximately ovate, or egg-shaped, when viewed from the distal end 122.

Figure 1C:
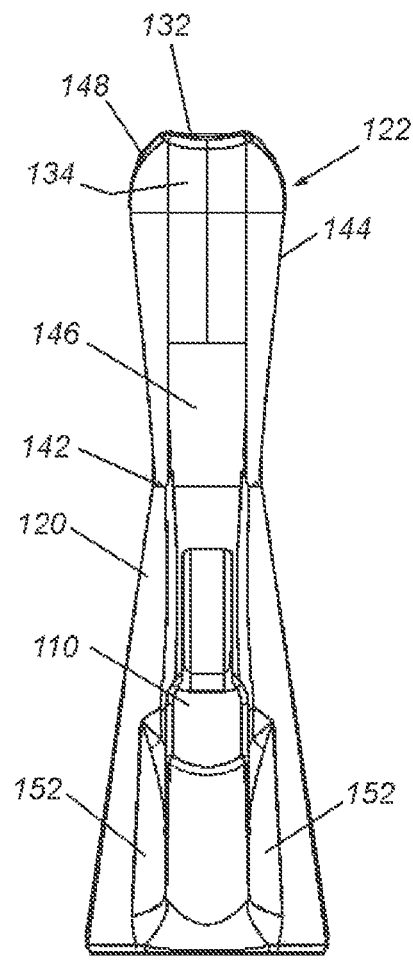
FIG. 1C is a top view of a laryngoscope, according to an embodiment.

FIG. 1C is a top view of a laryngoscope, according to an embodiment. The neck 142 of the insertion member 120 can be the narrowest portion of the insertion member 120, and the bell 144 can extend outwards from the neck 142, so that the insertion member becomes wider towards the distal end 122. The bell 144 can extend between the neck 142 and the rim 148. The rim 148 can be approximately in the shape of a cylindric section or tear-drop shaped, with a flattened area where the ramp 134 meets the rim 148. The laryngoscope 100 can have side filets 152 where the handle 110 meets the insertion member 120. The side fillets 152 can provide increased strength to the laryngoscope 100 at the union between the handle 110 and insertion member 120, so that the laryngoscope can withstand the forces imparted by the patient, while allowing the laryngoscope 100 to be made from a lightweight, non-metallic material that can be radiolucent A laryngoscope 100 can be manufactured using 3D printer, such as the Objet Eden250 manufactured by Stratasys, by way of non-limiting example of a variety of possible devices and modalities. The laryngoscope 100 can be manufactured from non-metallic materials that can be radiolucent, such as polymers including poly(methyl methacrylate) (acrylic), or polyethylene, polycarbonate, polyamide (nylon), and/or polyvinyl chloride. By manufacturing the laryngoscope 100 from non-metallic materials, the laryngoscope 100 can be used within MM scanners, CT scanners, PET scanners, X-rays, and other imaging devices, and can be used with electromagnetic instrument tracking. In some embodiments designed for use with MR imaging, ceramic material can also be used.

Figure 2A:
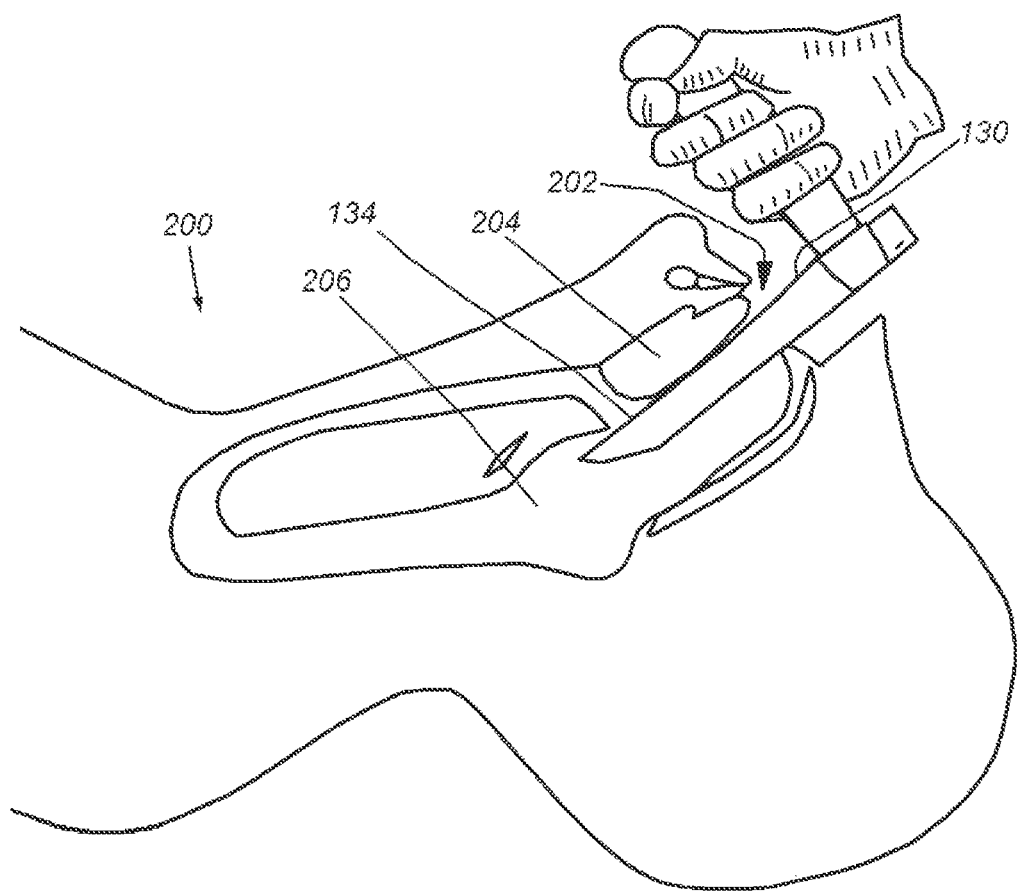
FIG. 2A is a diagrammatic view of a patient with a laryngoscope being inserted into the patient's mouth by a medical provider, according to an embodiment.
Figure 2B:
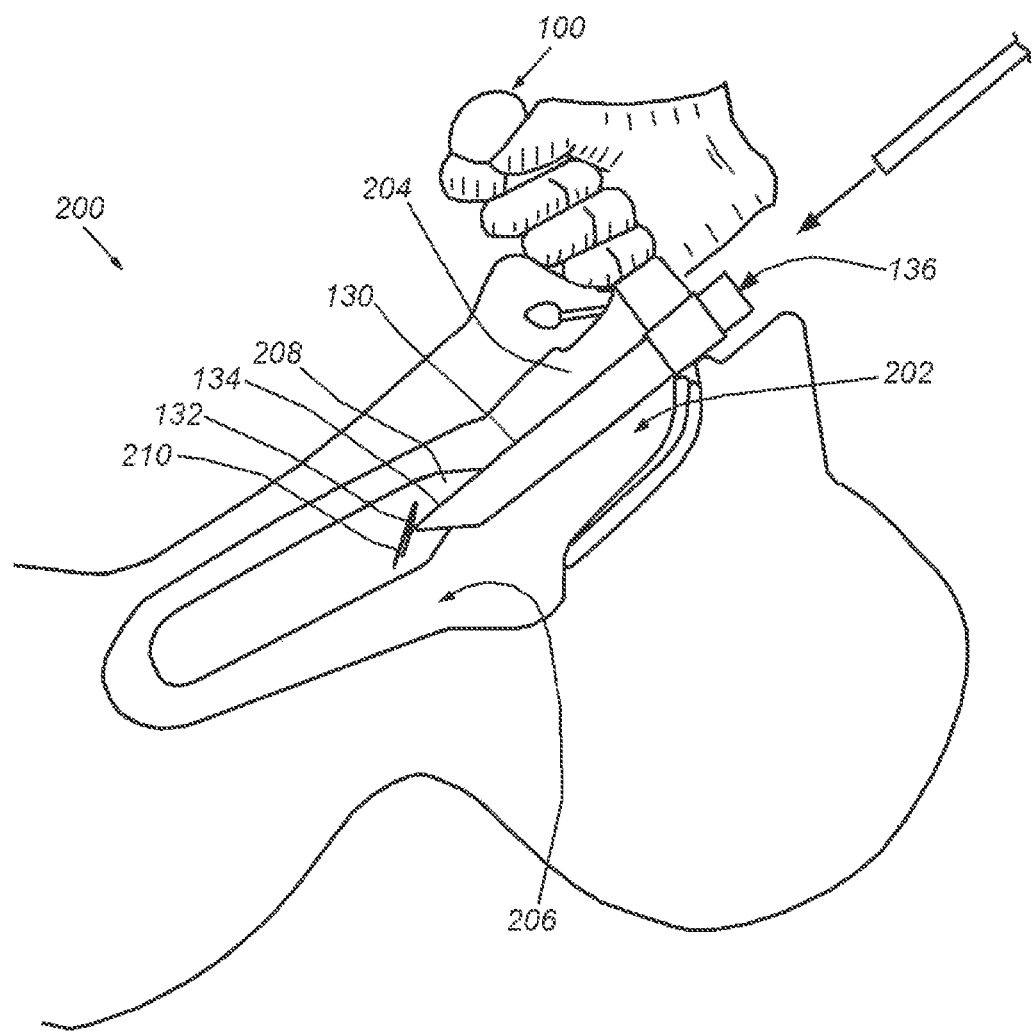
FIG. 2B is a diagrammatic view of a patient with a laryngoscope being inserted into the patient's throat by a medical provider, according to an embodiment.

FIG. 2A is a diagrammatic view of a patient with a laryngoscope being inserted into the patient's mouth by a user, such as a medical provider, according to an embodiment. A patient 200 can be positioned on his back, so that a medical provider can insert a laryngoscope 100. The medical provider can insert the laryngoscope 100 into the patient's mouth 202, and can use the blade 130 to move the tongue 204 up and/or off to one side so that the tongue can be out of the way, thereby providing an unobstructed view of the top of the patient's throat 206. The curve of the ramp 134 can be inserted down the patient's throat 206. FIG. 2B is a diagrammatic view of a patient with a laryngoscope being inserted into the patient's throat by a medical provider, according to the embodiment. The leading edge 132 and/or the ramp 134 can be used to lift the epiglottis 208 so that the medical provider can insert the laryngoscope 100 past the epiglottis 208 and down the throat 206. The patient can have his head tilted back, so that the medical provider can insert the laryngoscope 100 through the mouth 202 and into the throat 206. The laryngoscope can provide an unobstructed path between the outside of the patient and the anatomical structures in the patient's throat, such as the larynx 210, voice box, glottis, and or/other structures. With the laryngoscope inserted into the patient's throat, the medical provider can have a clear view of the larynx 210, voice box, glottis, and/or other structures through the central lumen 136. The medical provider can direct a laser or other surgical tool through the central lumen 136. The medical provider can insert an intubation tube into the patient through the central lumen 136.

A laryngoscope can be used by a medical provider who can perform surgery on the patient, such as surgery directed to a tumor in the throat or other anatomical structure. A patient can be sedated while the laryngoscope 100 is inserted into the throat 206 so that the user can see into the throat and can direct a laser or other surgical tool into the throat 206. When the patient is sedated with his head tilted back, and with a laryngoscope in the throat 206, the patient's anatomical structures such as the larynx and other structures of the throat, as well as tumors or other areas to be targeted for surgery, can shift positions. Images taken of the anatomical structures, including possible tumors, while the patient is awake and/or in a more common position may not accurately reflect the locations of anatomical structures and tumors while the patient is sedated, with the head tilted back and the laryngoscope inserted in the throat. The laryngoscope 100 that is made of non-metallic materials can be used in an MRI scanner, CT scanner, or other imaging devices. A user can use the imager to obtain images of the patient's anatomical structures while the laryngoscope is inserted, so that the user can accurately perform surgery on the correct areas, such as the area of a tumor.

Figure 3A:
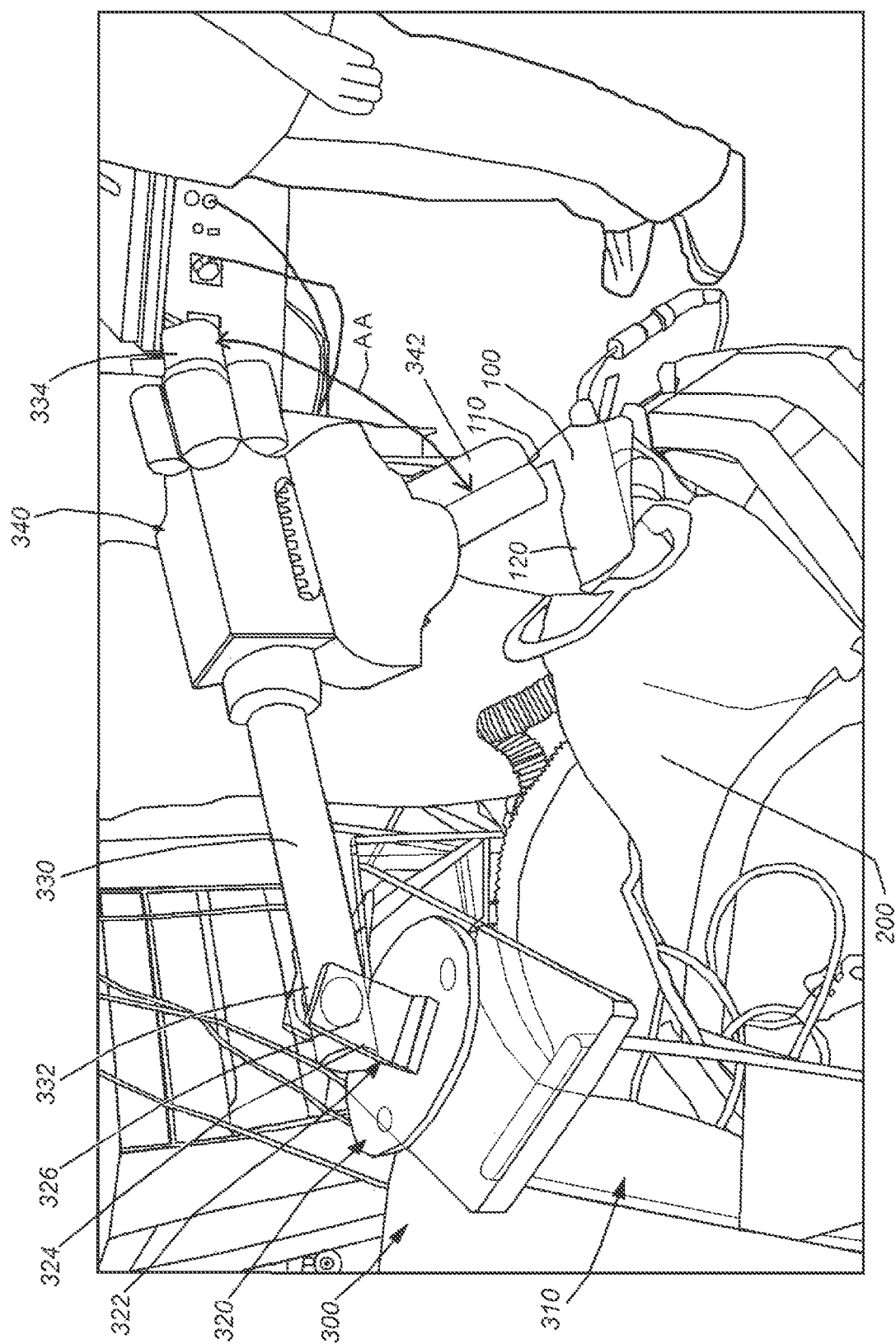
FIG. 3A is a perspective view of a patient with an inserted laryngoscope, with the laryngoscope held in a support rig, according to an embodiment.

FIG. 3A is a perspective view of a patient with an inserted laryngoscope, with the laryngoscope held in a support rig, according to an embodiment. A support rig 300 can hold a laryngoscope 100 in a fixed position and orientation, without the user needing to hold the laryngoscope 100. The support rig 300 can maintain the laryngoscope 100 in a fixed position and orientation without being impacted by breathing or other movement of the patient 200. A support rig 300 can have a frame 310, a wrist 320, an arm 330, and an elbow assembly 340. A frame 310 can provide a base for the support rig 300, so that the laryngoscope 100 can be supported above the patient and not be affected by breathing or other movements of the patient 200.

Figure 3B:
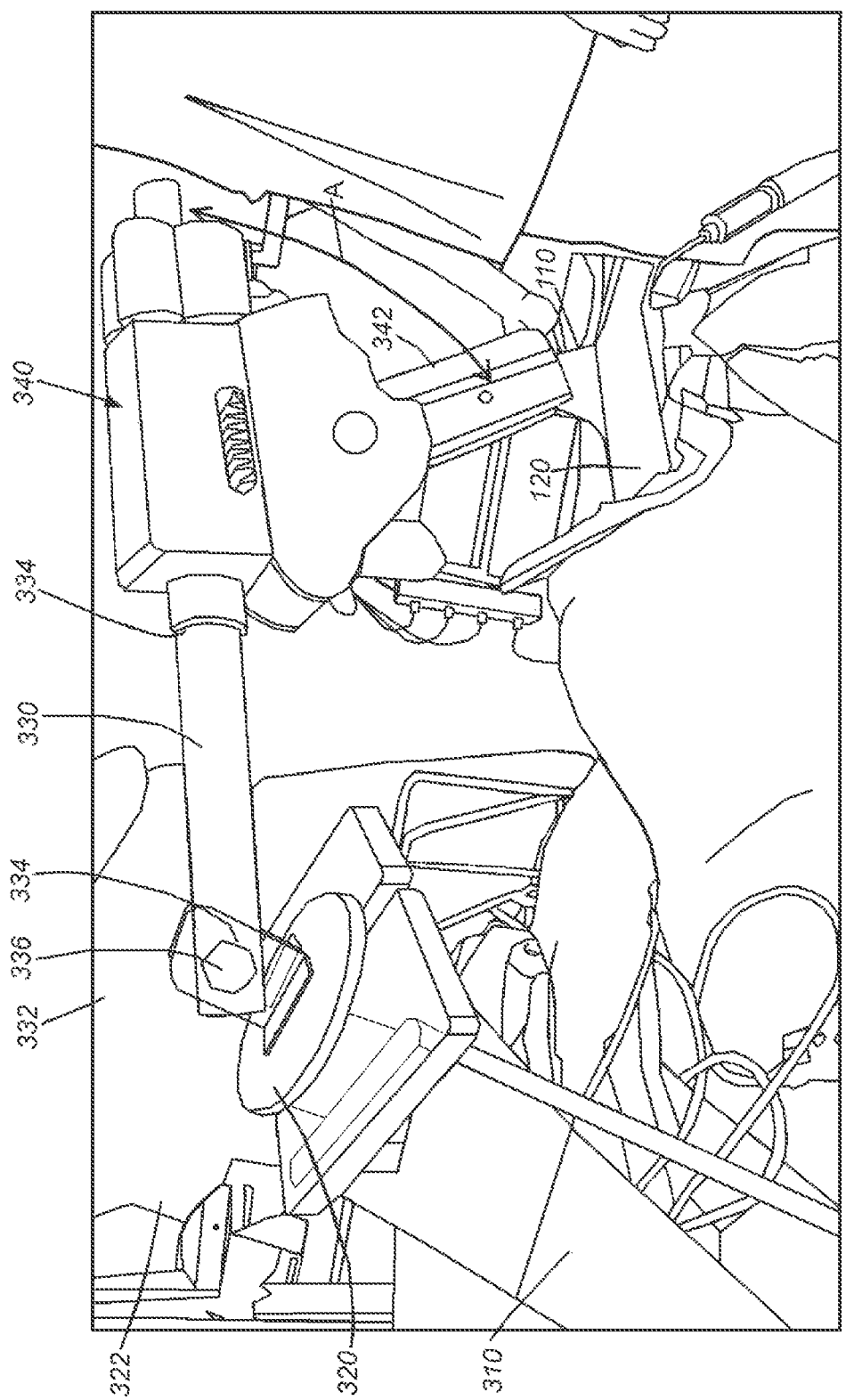
FIG. 3B is a side view of a patient with an inserted laryngoscope, with the laryngoscope held in a support rig, according to the embodiment.

FIG. 3B is a side view of a patient with an inserted laryngoscope, with the laryngoscope held in a support rig, according to the embodiment. A wrist 320 can be mounted to the frame 310. In various embodiments the wrist 320 can be held in a fixed position relative to the frame 310, or the wrist 320 can swivel relative to the frame 310. In various embodiments the wrist 320 can swivel freely relative to the frame 310, or the user can swivel the wrist 320 into a selected orientation and can fix the wrist 320 into the selected orientation relative to the frame 310.

The arm 330 can be hingedly mounted to the wrist 320. The arm 330 can have a wrist area 332 and an elbow area 334, and the arm 330 can be hingedly mounted to the wrist 320 at the wrist area 332. The wrist 320 can have a hinge 322. The hinge can have at least one arm holder 324 and a pin 326. The at least one arm holder 324 can extend from the wrist 320 and can have at least one hinge hole through the arm holder 324. The arm 330 can have a hinge hole at the wrist area 332. A pin 326 can pass through the arm holder 324 and the wrist area 332 of the arm. The pin 326 can be a bolt or other connector that can pass through the hinge hole in the arm 330 and the hinge hole in the arm holder 324, so that the arm 330 can pivot on the hinge 322. In alternate embodiments, various different hinges can be used, and should be obvious to one of skill in the art. A user can adjust the position and orientation of the arm 330 relative to the frame 310 by pivoting the arm 330 on the hinge 322. A user can adjust the position and orientation of the arm 330 relative to the frame 310 by swiveling the wrist 320.

An elbow assembly 340 can be connected to the arm 330. An elbow assembly 340 can have a holder 342. The holder 342 can hold the handle 110 of the laryngoscope 100, so that the handle 110 can be fixed to the holder 342. The elbow assembly 340 can allow a user to adjust the elbow angle HA, which is the angle of the handle 110 relative to the arm 330. The elbow assembly 340 can allow the user to set the angle of the handle 110 relative to the arm 330 in a fixed orientation, explained more fully below.

The angle or orientation of the insertion member 120 can be changed by adjusting the elbow angle HA of the handle 110 to the arm 330 because the rigid laryngoscope 110 can have the insertion member 120 and the handle 110 at a fixed angle relative to each other. When a user adjusts the elbow angle, the angle and orientation of the entire laryngoscope 100, including the insertion member 120 can be adjusted. The distal end of the insertion member 120 can remain inserted in the throat while the user adjusts the angle and orientation of the insertion member 120 by adjusting the elbow angle. When the insertion member 120 is inserted in the throat and the elbow angle is adjusted, the arm 330 can pivot on the hinge 322.

A user can insert the insertion member 120 into a patient, and the user can affix the handle 110 to the holder 342. The user can then adjust the elbow angle to adjust the orientation of the insertion member 120. By adjusting the orientation of the insertion member 120, the user can move the insertion member 120 into a desired position to see a particular anatomical structure within the patient's throat. Adjusting the orientation of the insertion member can allow a user to position the lumen at a preferred angle for directing a laser or other surgical instrument through the lumen towards targeted anatomical structure. In an embodiment, a metallic insert, such as a metallic tube, can be removably placed within the central lumen 136 of the insertion member 120 to shield the laryngoscope form the laser. A user can insert the metallic insert for use with the laser, and the user can remove the metallic insert prior to imaging.

Figure 3C:
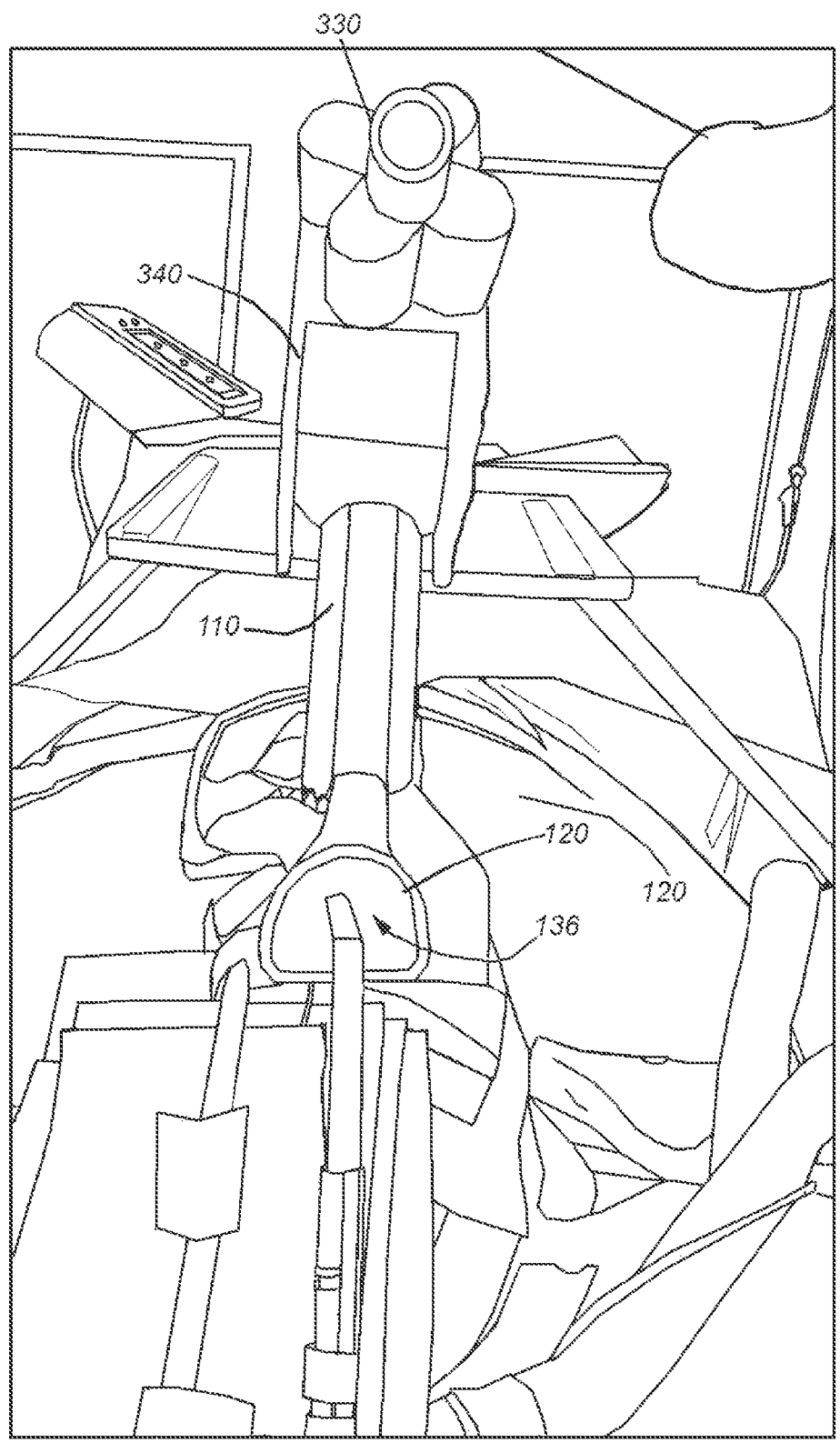
FIG. 3C is an end view of a patient with an inserted laryngoscope, with the laryngoscope held in a support rig, according to the embodiment.

FIG. 3C is an end view of a patient with an inserted laryngoscope, with the laryngoscope held in a support rig, according to an embodiment. The laryngoscope is shown inserted into the throat and holding the tongue to the side. A user can direct a light through the lumen 136 and can look through the lumen to see the anatomical structures such as the larynx. A user can direct a laser through the lumen towards anatomical structures such as the larynx. A user can adjust the angle of the insertion member 120 and lumen 136 so that the user can have a desired view or a desired angle for a laser or other surgical instrument. The user is able to fix the insertion member 120 at a desired angle that will not be changed by the breathing or other movement of the patient 200.

Figure 4A:
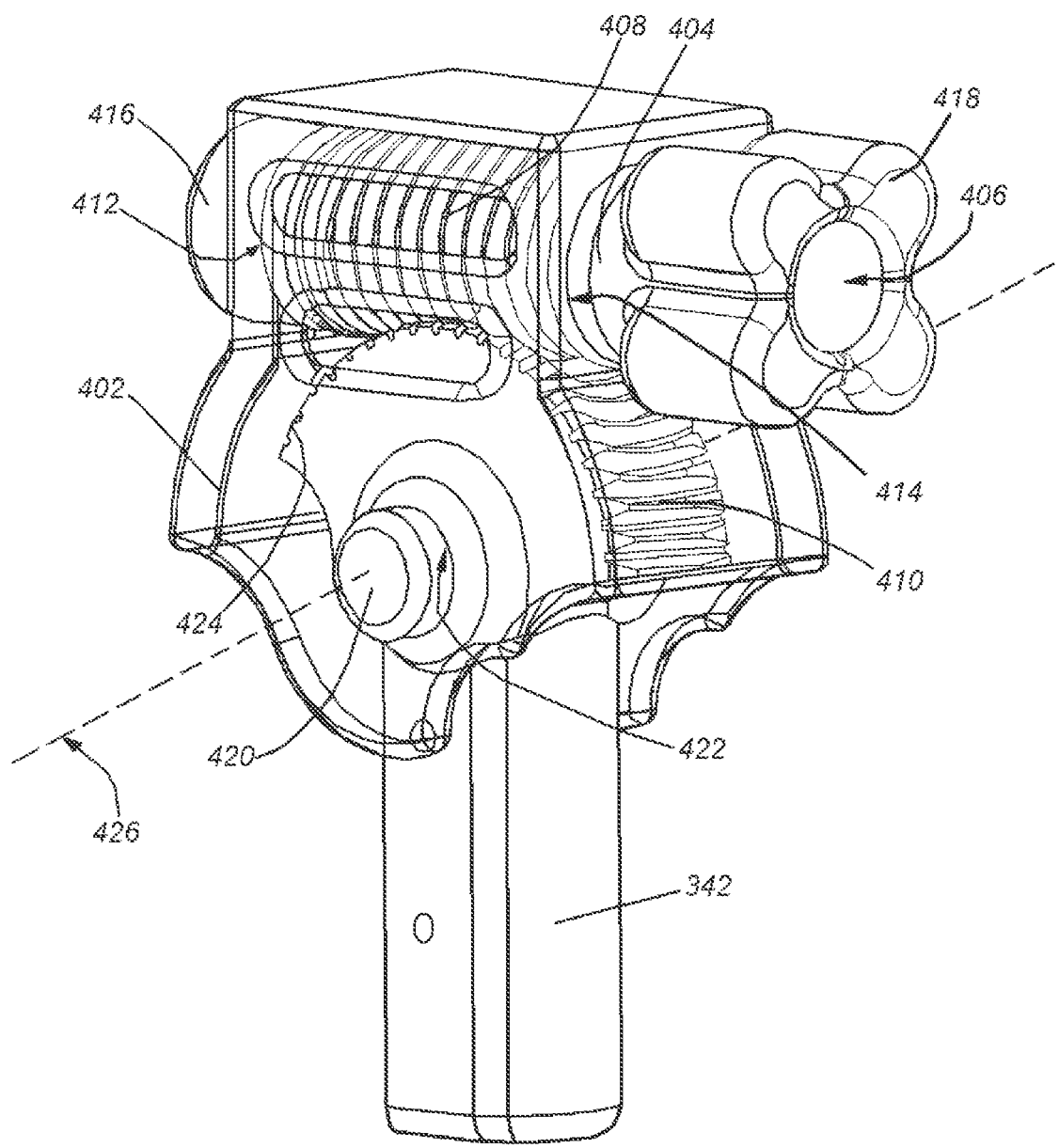
FIG. 4A is a perspective view of an elbow assembly, according to an embodiment.

FIG. 4A is a perspective view of an elbow assembly, according to an embodiment. An elbow assembly can allow a user to adjust the orientation of a laryngoscope that is inserted into the throat of a patient. It should be clear that the elbow assembly can be used with a laryngoscope and/or various other retractors or other surgical instruments without departing from the scope of the present disclosure. A user can fine tune the angle of the laryngoscope and fix the angle to that it remains in the selected position. An elbow assembly can have an outer shell 402, an adjuster 404, and a holder 342. The elbow assembly 340 can have a bore 406. The bore 406 can be an opening in the elbow assembly 340 adapted to engage with the arm. The bore 406 can be through the adjuster 404. The arm can be inserted through the bore 406, and the adjuster 404 can rotate on the arm 330. In alternate embodiments, the elbow assembly can clip onto the arm or otherwise be attached to the arm in various ways that will be apparent to one skilled in the art.

The elbow assembly 340 can have a worm gear 408 and a rack 410. The worm gear 408 can be on the adjuster 404 and the rack 410 can be on the holder 342. The outer shell 402 can hold the worm gear 408 in engagement with the rack 410. The outer shell can have a distal opening 412 and a proximal opening 414. The adjuster can have a distal extension 416 and a knob 418. The distal extension 416 can protrude through the distal opening 412, and the knob 418 can protrude through the proximal opening 414, so that the adjuster 404 can be held within the outer shell 402, and can rotate in place within the outer shell 402. The elbow assembly can have at least one axle 420. The at least one axle 420 can be a part of the holder 342 that extends from the holder 342 and can be engaged by the outer shell 402, so that the holder can pivot relative to the outer shell 402 on the axle 420. The at least one axle 420 can extend through at least one side opening 422 through the outer shell 402. The at least one axle 420 can be an independent axle that can extend through the holder 342 and be engaged by the outer shell 402, so that the holder 342 can pivot relative to the outer shell 402 on the axle 420.

The holder 342 can have an upper arc 424 that can be a segment of a cylinder with a central axis 426 that passes through the axle 420. The rack 410 can be arranged along the circumference of the upper arc 424, so that teeth of the rack 410 can be equidistant from the central axis that passes through the axle 420. A user can turn the knob 418, which can cause the adjuster 404 to rotate within the outer shell 402 and turn the worm gear 408. The turning worm gear 408 can cause the rack 410 to rotate around the central axis, with the holder turning on the at least one axle 420. When the user turns the knob 418, causing the holder 342 to turn on the at least one axle 420, the angle between the holder 342 and the arm 330 (not shown) can be changed.

Figure 4B:
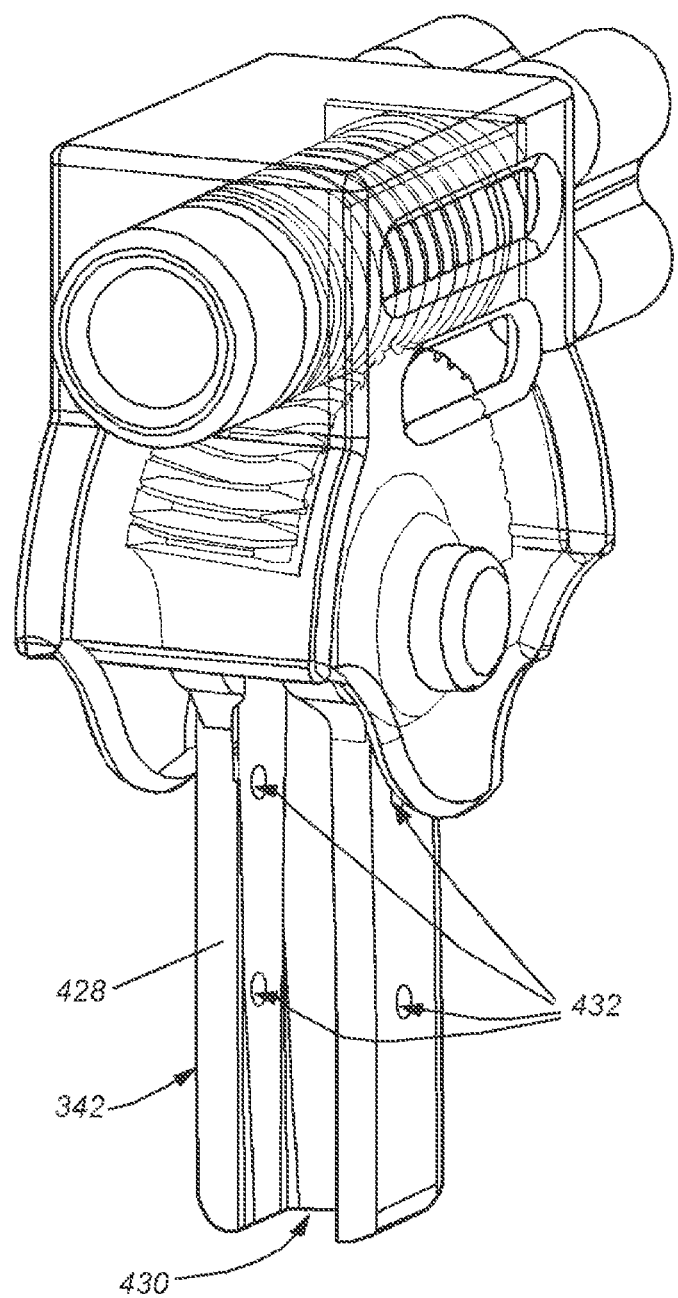
FIG. 4B is a perspective view of an elbow assembly from a different perspective, according to the embodiment

FIG. 4B is a perspective view of an elbow assembly from a different perspective, according to the embodiment. The holder 342 can have an engagement arm 428 adapted to engage with the handle. The engagement arm 428 can have an engagement area 430. The engagement area 430 can be a channel in the engagement arm 428. The channel can be sized and shaped to be adapted for the handle 110 to be placed within the channel. The engagement arm 428 can have at least one securing hole 432. The at least one securing hole 432 can be aligned with at least one securing hole 114 of the handle 110, so that a bolt, pin, or other securing means can be passed through the securing hole 432 of the holder and the securing hole 114 of the handle, thereby securing the handle within the engagement area 430.

Figure 4C:
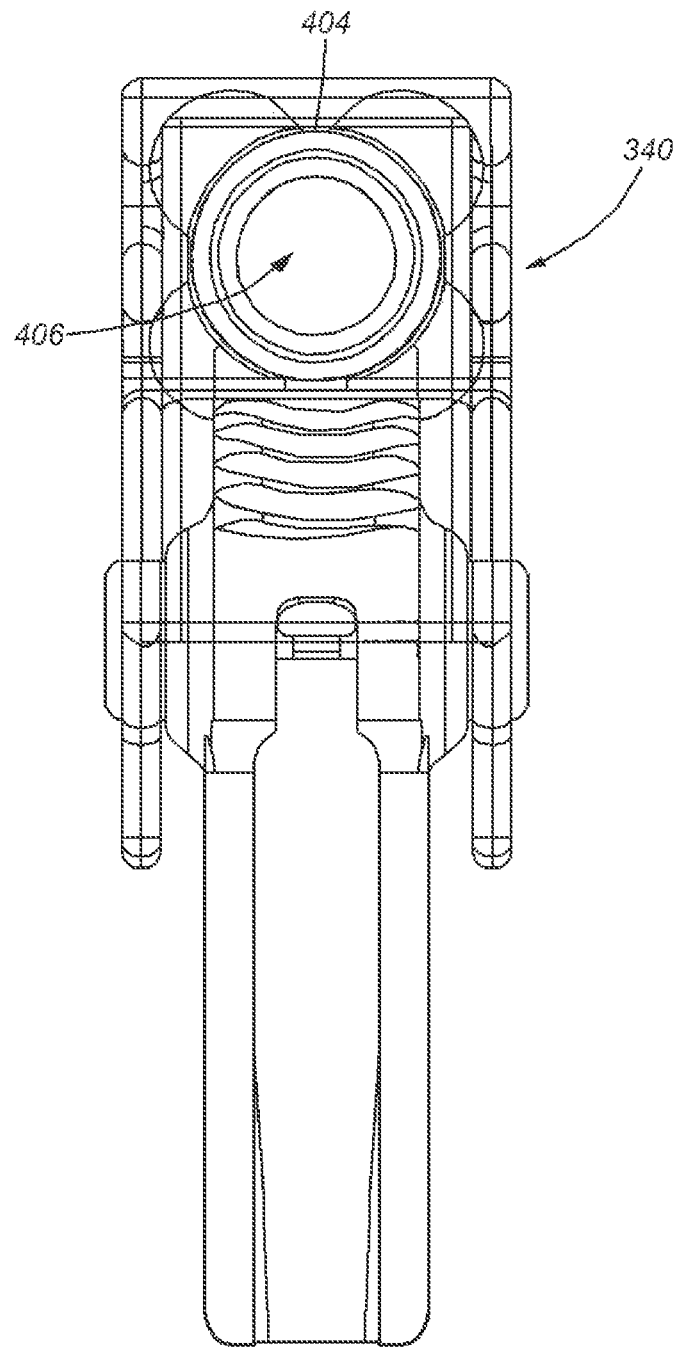
FIG. 4C is an end view of an elbow assembly, according to the embodiment.

FIG. 4C is an end view of an elbow assembly, according to the embodiment. The bore 406 can be an opening in the elbow assembly 340. The bore 406 can have a shape that is adapted to the shape of the elbow end 334 of the arm 330, so that arm 330 can be inserted into the bore 406. In the embodiment, the arm 330 can be cylindrical, and the bore 406 can be cylindrical and can be through the adjuster 404, so that the adjuster 404 can rotate around the arm 330.

Figure 4D:
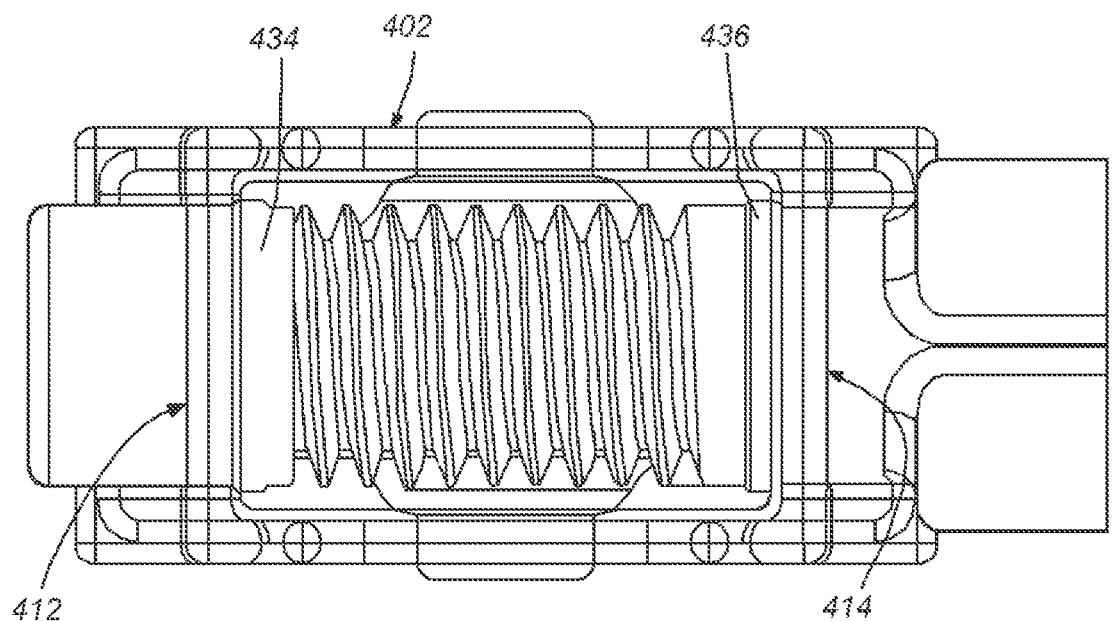
FIG. 4D is a top view of an elbow assembly, according to the embodiment.

FIG. 4D is a top view of an elbow assembly, according to the embodiment. The adjuster 404 can have a distal ridge 434 and a proximal ridge 436. The distal ridge 434 can be larger than the distal opening 412 of the outer shell 402, so that the distal ridge 434 does not pass through the distal opening 412. The proximal ridge 436 can be larger than the proximal opening 414 of the outer shell 402, so that the proximal ridge 436 does not pass through the proximal opening 414. The distal ridge 434 and proximal ridge 436 can hold the adjuster 404 within the outer shell 402.

In an embodiment, the elbow assembly 140 can be printed using a 3D printer such as the Objet Eden250 manufactured by Stratasys. 3D printing the elbow assembly can allow all of the parts to be printed together at the same time, so that the finished elbow assembly is already assembled when the printing is finished. In this way, an adjuster 404, which can include a proximal ridge 436 and/or a distal ridge 434, can be printed within the outer shell 402 in the same printing session as the outer shell 402 is printed, so that there is no need to assemble the various components of the elbow assembly within the outer shell 402 after the components are printed. After printing of the outer shell 402 has begun, but before printing of the outer shell has been completed, other components of the elbow assembly 340 can be printed within the uncompleted outer shell 402, so that the finished printed product can be a fully assembled elbow assembly.

Figure 5A:
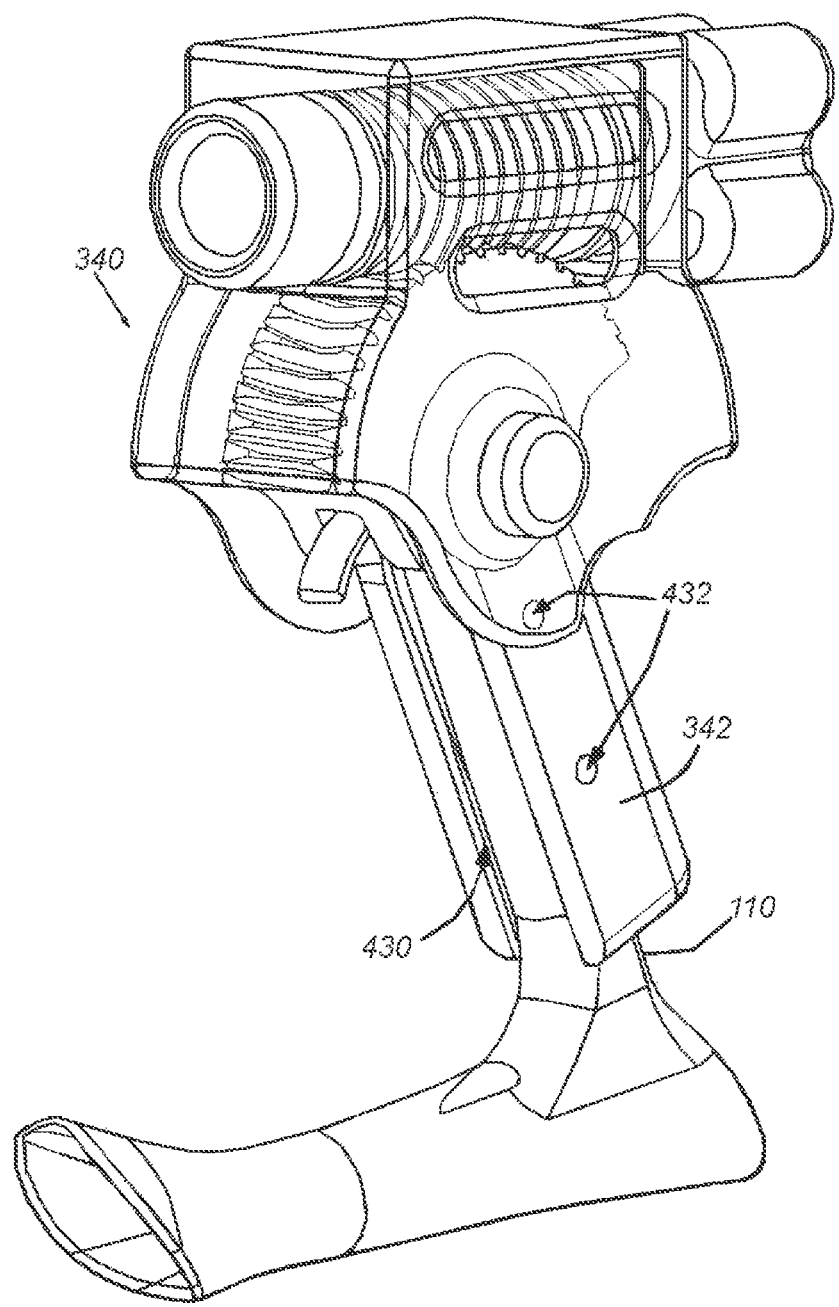
FIG. 5A is a perspective view of an elbow assembly with a laryngoscope, according to an embodiment.

FIG. 5A is a perspective view of an elbow assembly with a laryngoscope, according to an embodiment. The handle 110 of a laryngoscope 100 can be engaged with the holder 342. In the embodiment, the handle 110 can be inserted in an engagement area 430 of the holder 342. The at least one securing hole 432 of the holder can be aligned with the at least one securing hole 114 of the handle. A bolt, pin, screw, or other securing means can be inserted through the holder and the handle, thereby securing the handle 110 to the holder 342. The bolt, pin, screw, or other securing means can be non-metallic and can be made out of a polymer. The handle 110 can be secured to the holder 342 in a fixed relationship.

Figure 5B:
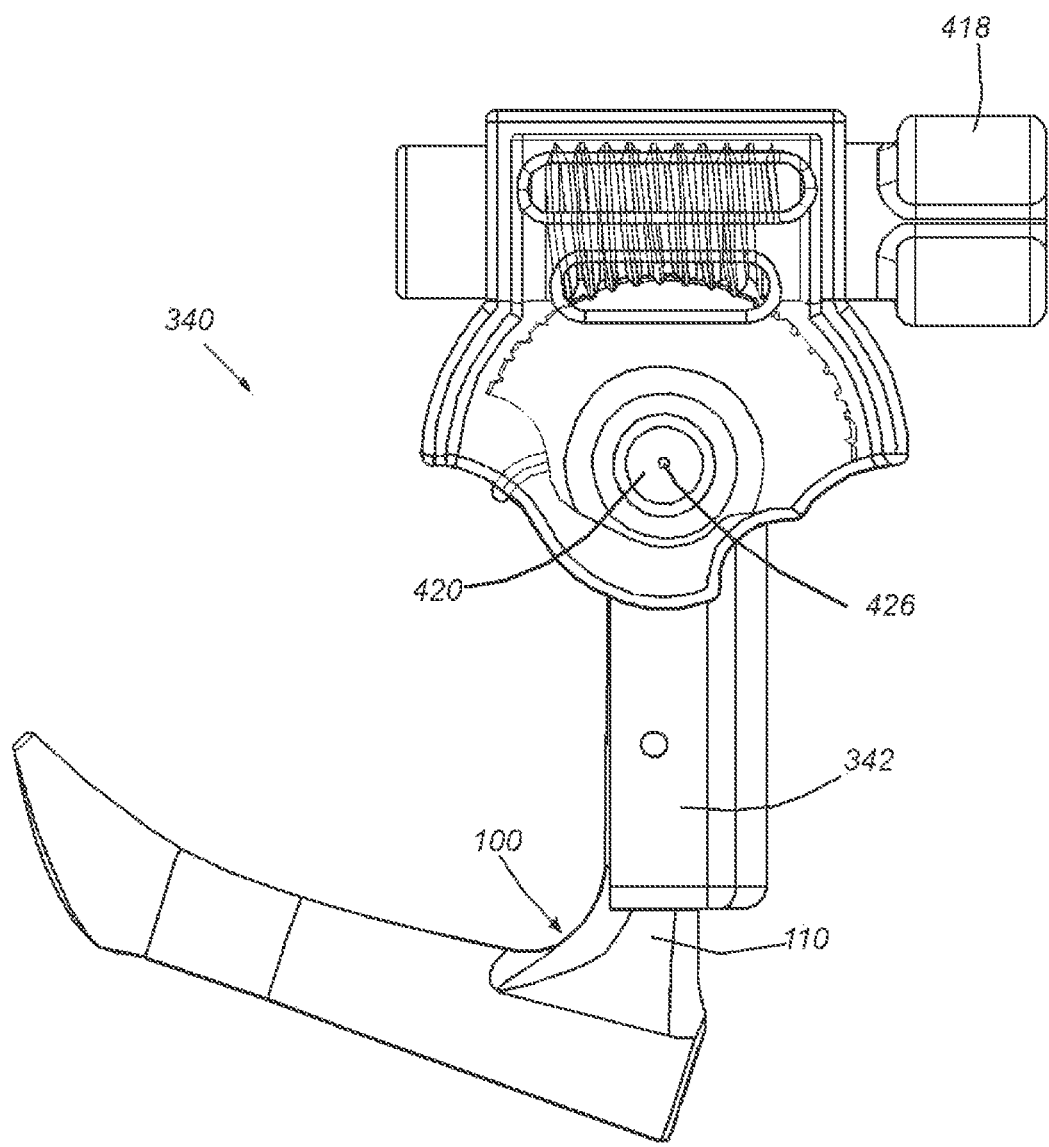
FIG. 5B is a side view of an elbow assembly with a laryngoscope, according to the embodiment.
Figure 5C:
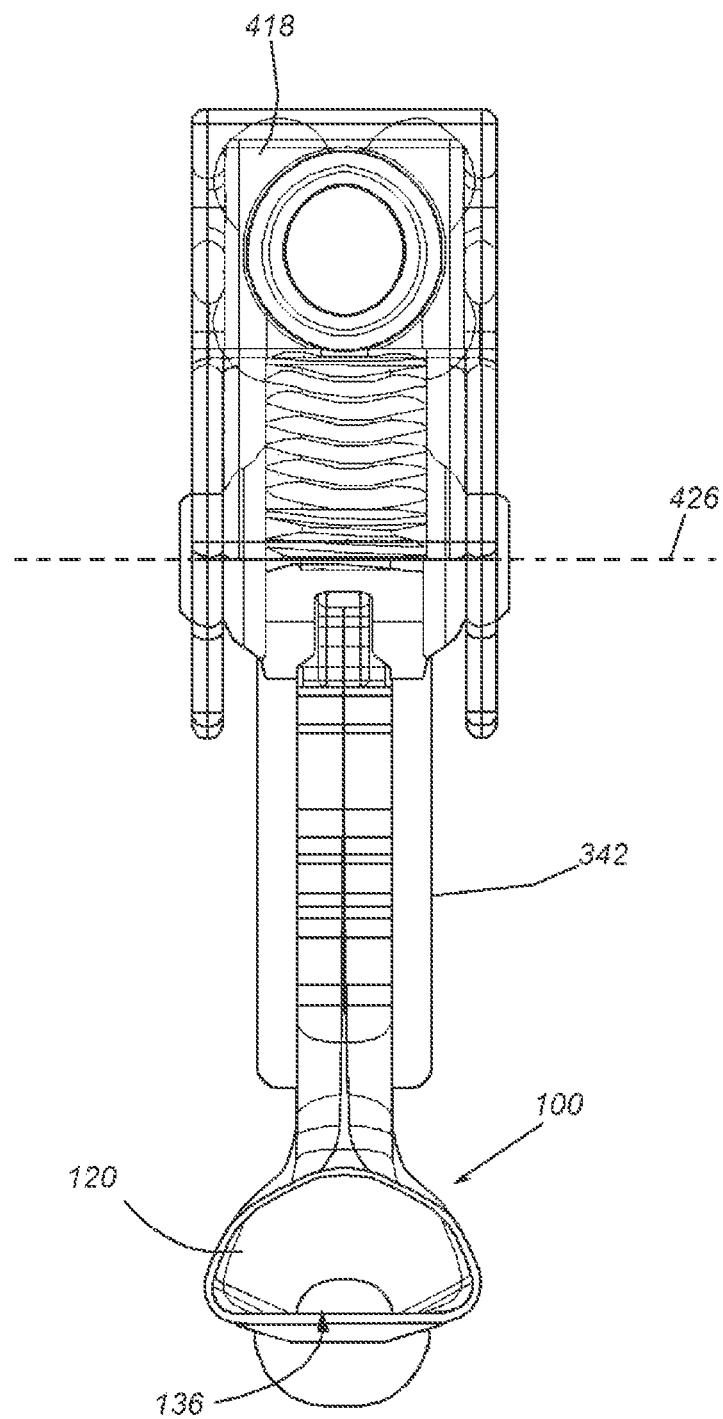
FIG. 5C is an end view of an elbow assembly with a laryngoscope; according to an embodiment.

FIG. 5B is a side view of an elbow assembly with a laryngoscope, according to the embodiment. When a user turns the knob 418, the holder can rotate around the central axis 426 on the axle 420. The handle 110 can be secured to the holder 342 in a fixed relationship, and the laryngoscope 100 can move unitarily with the holder 342. FIG. 5C is an end view of an elbow assembly with a laryngoscope; according to the embodiment. The orientation of the insertion member 120 can be adjusted by turning the knob 418, causing the holder 342 and attached laryngoscope 100 to rotate around the central axis 426. A user can turn the knob 418 to adjust the orientation of the insertion member 120, thereby allowing the user to move the insertion member 120 into a desired position so that the user can look through the central lumen 136 at a desired orientation for viewing anatomical structures of the patient, such as the larynx.

Figure 6A:
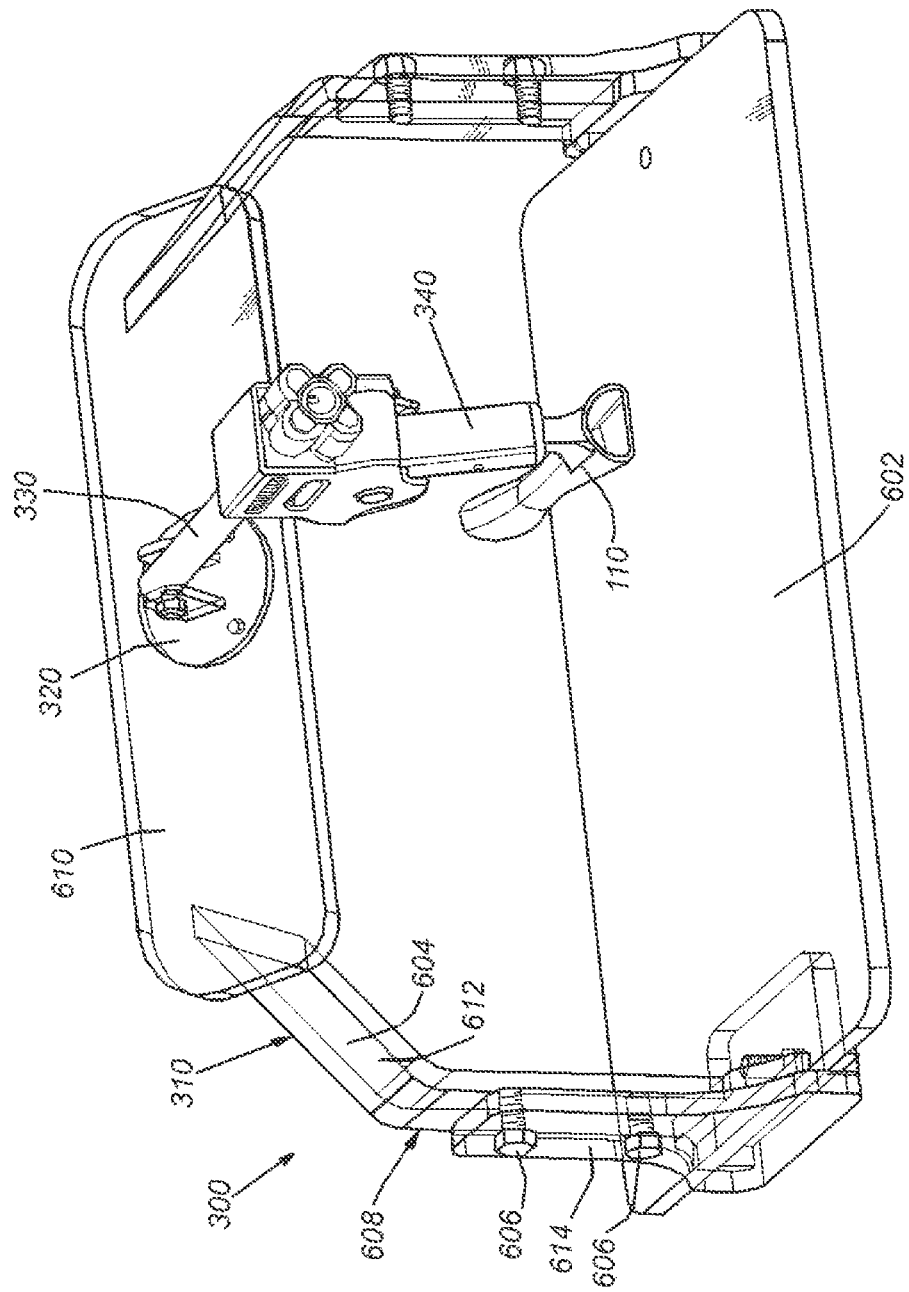
FIG. 6A is a perspective view of a support rig with an attached laryngoscope, according to an embodiment.

FIG. 6A is a perspective view of a support rig with an attached laryngoscope, according to an embodiment. The support rig 300 can have a frame 310, a wrist 320, an arm 330, and an elbow assembly 340, and a laryngoscope 100 can be mounted to the elbow assembly 340. It should be clear that the support rig 300 can be used with a laryngoscope and/or various retractors or other surgical instruments without departing from the scope of the present disclosure. The frame 310 can have a patient platform 602 and a tower 604. The tower 604 can be attached to the platform 602 with at least one tower bolt 606, or other means such as adhesives or welding, including plastics welding. In various embodiments, the patient platform 602 can a patient's bed, and the tower 604 can be attached directly to a portion of the patient's bed in one at one or more areas of the patent's bed, for example a bed frame, side rail, or other areas of the patent's bed. The tower 604 can extend upwards from the platform 602, and the wrist 320 can be mounted to the tower 604. The tower 604 can support components of the rig 300 above the patient, so that movements of the patient do not affect the position and orientation of the laryngoscope 100 that can be attached to the rig 300. The frame 310 can be placed on an operating table, imaging table, or other patient support surface. A patient can be positioned on the platform 602. The weight of the patient 200 can help to hold the support rig 300 in position on a patient surface, so that the laryngoscope 100 can be maintained in a desired position and orientation relative to the patient.

The tower 604 can have at least one leg 608 and a cross member 610. The at least one leg 608 can have an upper leg 612, a lower leg 614, and at least one leg bolt 616. In some embodiments, the height of the tower 604 can be adjustable by removing the at least one leg bolt 618, and extending the upper leg 612 into a desired position relative to the lower leg 614, and inserting the at least one leg bolt 618 to secure the upper leg 612 to the lower leg 614. The cross member 610 can be attached to the at least one leg 606, and the cross member 610 can extend over the patient. The wrist 320 can be mounted to the cross member 610, so that it can be above the patient. In alternate embodiments, the tower 604 can be arch-shaped or other shapes, and can connect to the platform in at least one place, so that the wrist 320 can be suspended from the tower 604. A user can remove all or part of the tower 604, and can then position the patient onto the platform 602, and then assemble the frame 310, including the tower 604, after the patient has been positioned.

Figure 6B:
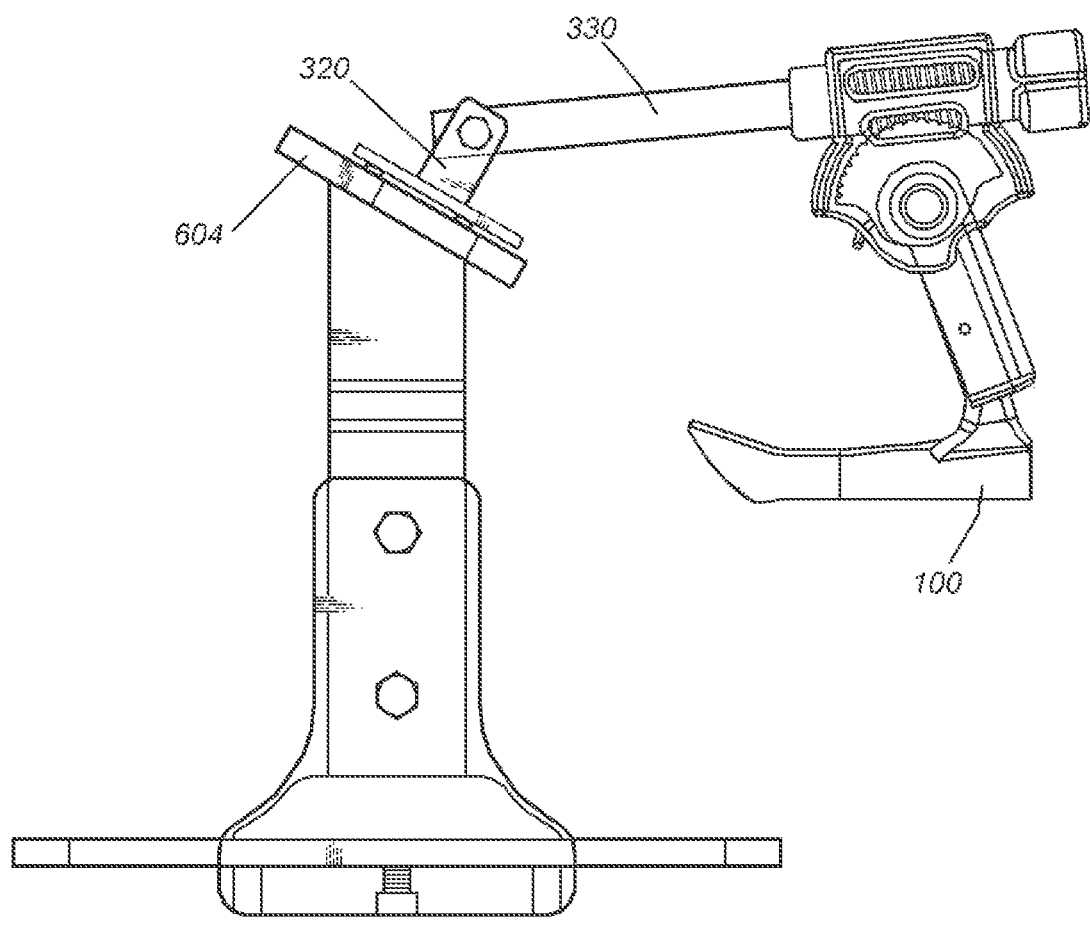
FIG. 6B is a side view of a support rig with an attached laryngoscope, according to the embodiment.

FIG. 6B is a side view of a support rig with an attached laryngoscope, according to the embodiment. The laryngoscope 100 can be maintained in a fixed orientation with the arm 330. The arm 330 can be hingedly mounted to the wrist 320 that is mounted to the tower 604. The tower 604 can support the wrist 320 and arm 330 above a patient.

Figure 6C:
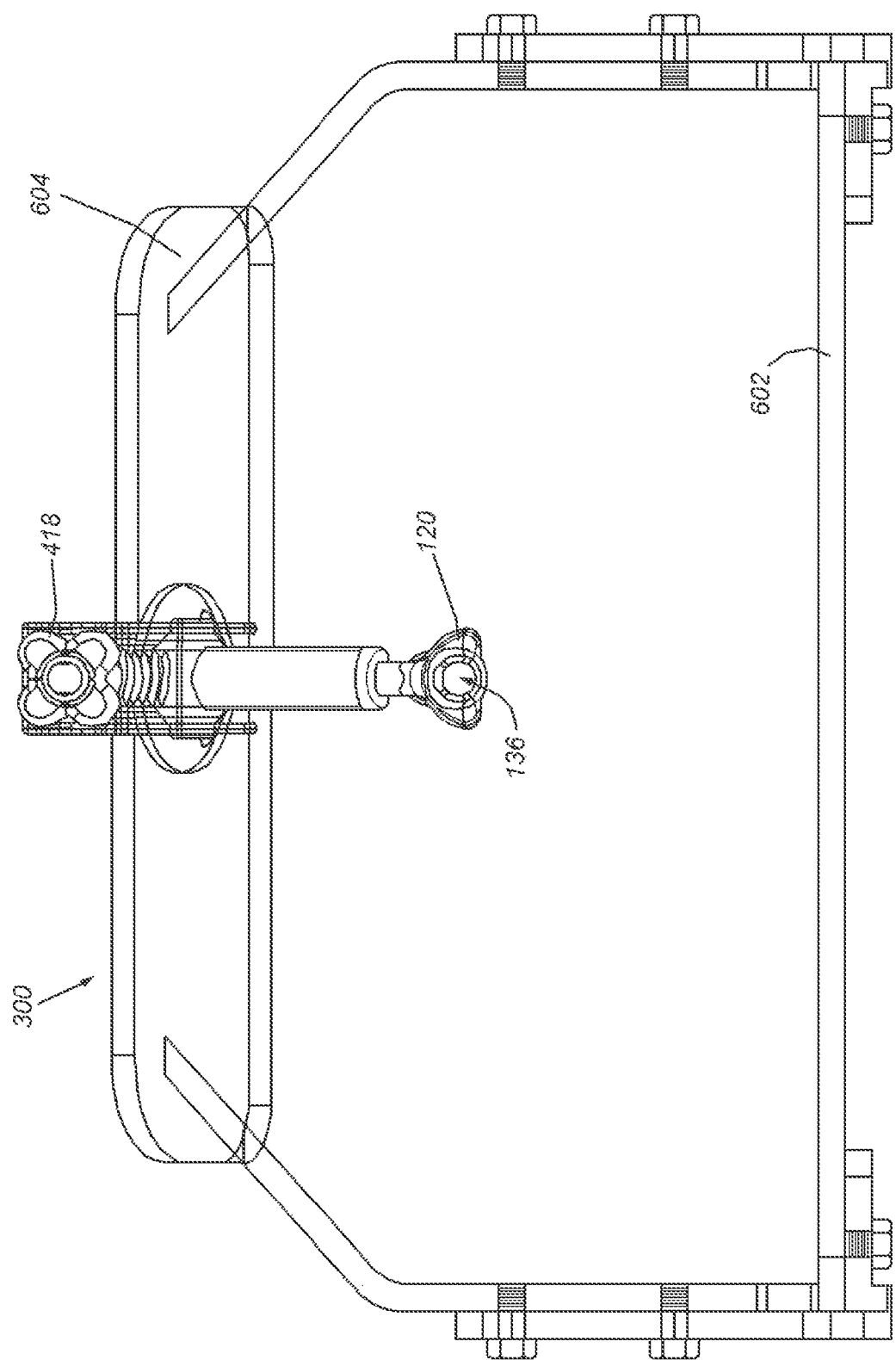
FIG. 6C is an end view of a support rig with an attached laryngoscope, according to the embodiment.
Figure 6D:
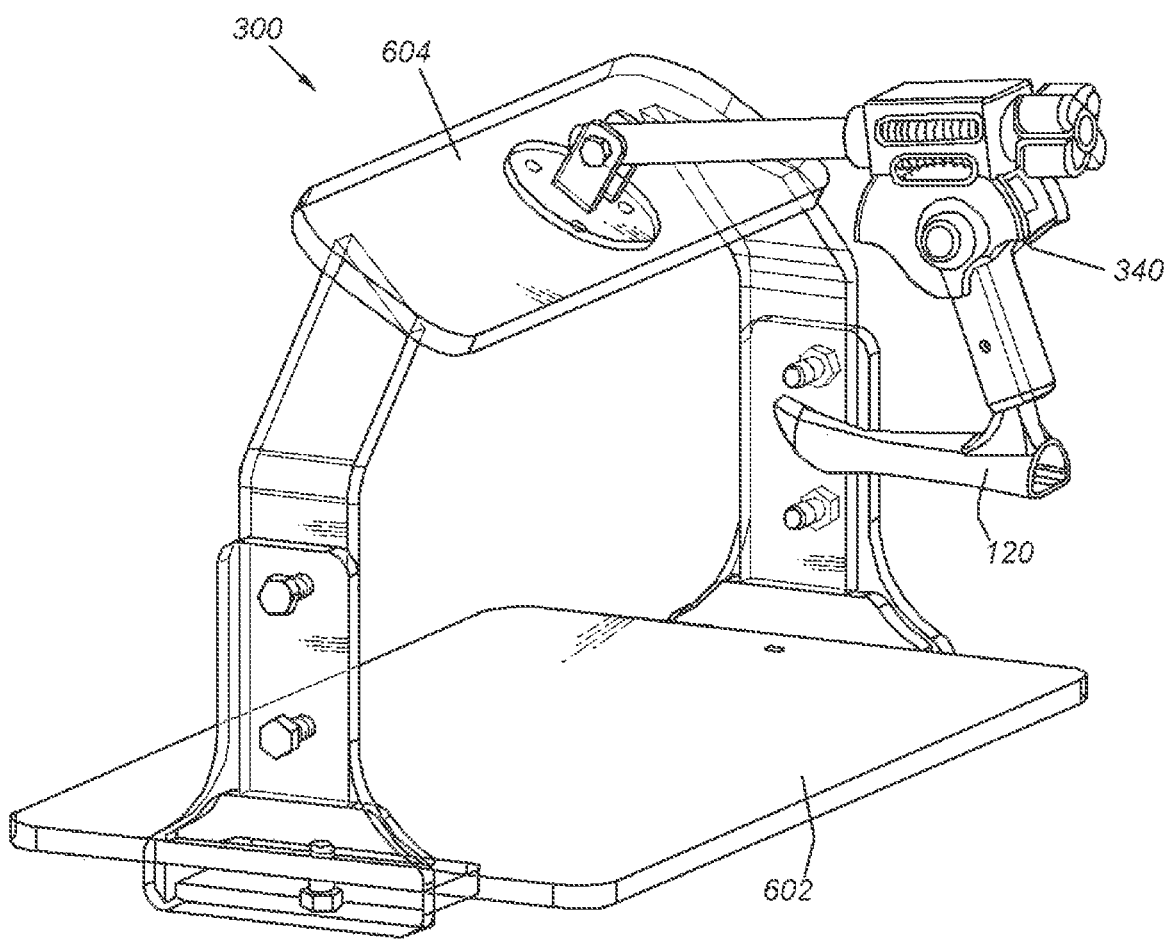
FIG. 6D is a perspective view of a support rig with an attached laryngoscope from an alternate perspective, according to the embodiment.

FIG. 6C is an end view of a support rig with an attached laryngoscope, according to the embodiment. A user can adjust the orientation of the insertion member 120 by turning the knob 418. Turning the knob 418 can adjust the angle of the central lumen 136, so that the user can look through the central lumen 136 and view the larynx or other anatomical structures of the patient at a desired angle. FIG. 6C depicts the central lumen 136 at an appropriate angle for a user to look through the central lumen from the given perspective. FIG. 6D is a perspective view of a support rig with an attached laryngoscope from an alternate perspective, according to the embodiment. The support rig 300 can support a laryngoscope that has been inserted into a patient (not shown), so that the laryngoscope can be maintained in a desired orientation relative to the patient that is not affected by breathing or other movements of the patient.

Figure 7A:
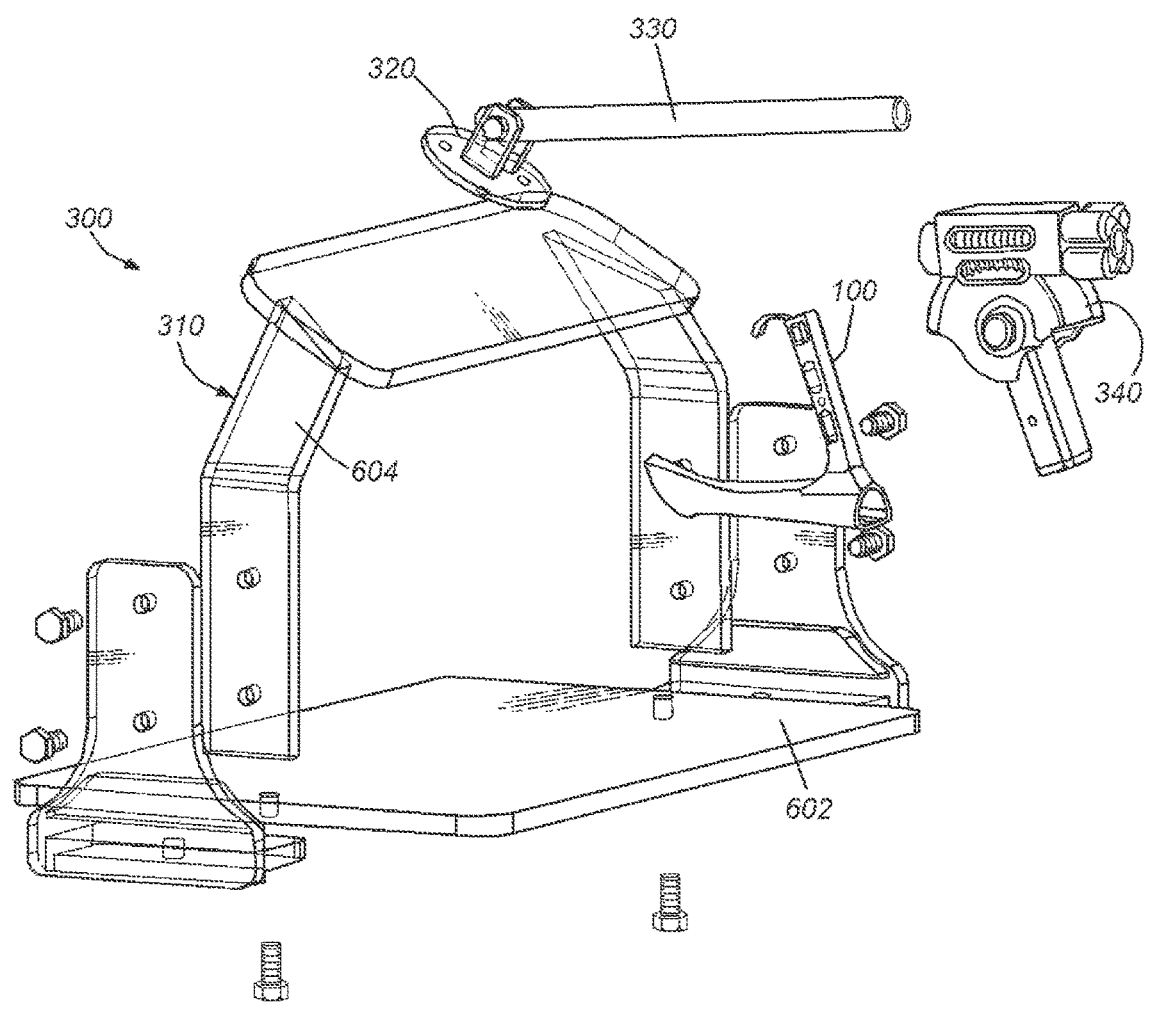
FIG. 7A is an exploded perspective view of a support rig and a laryngoscope, according to an embodiment.
Figure 7B:
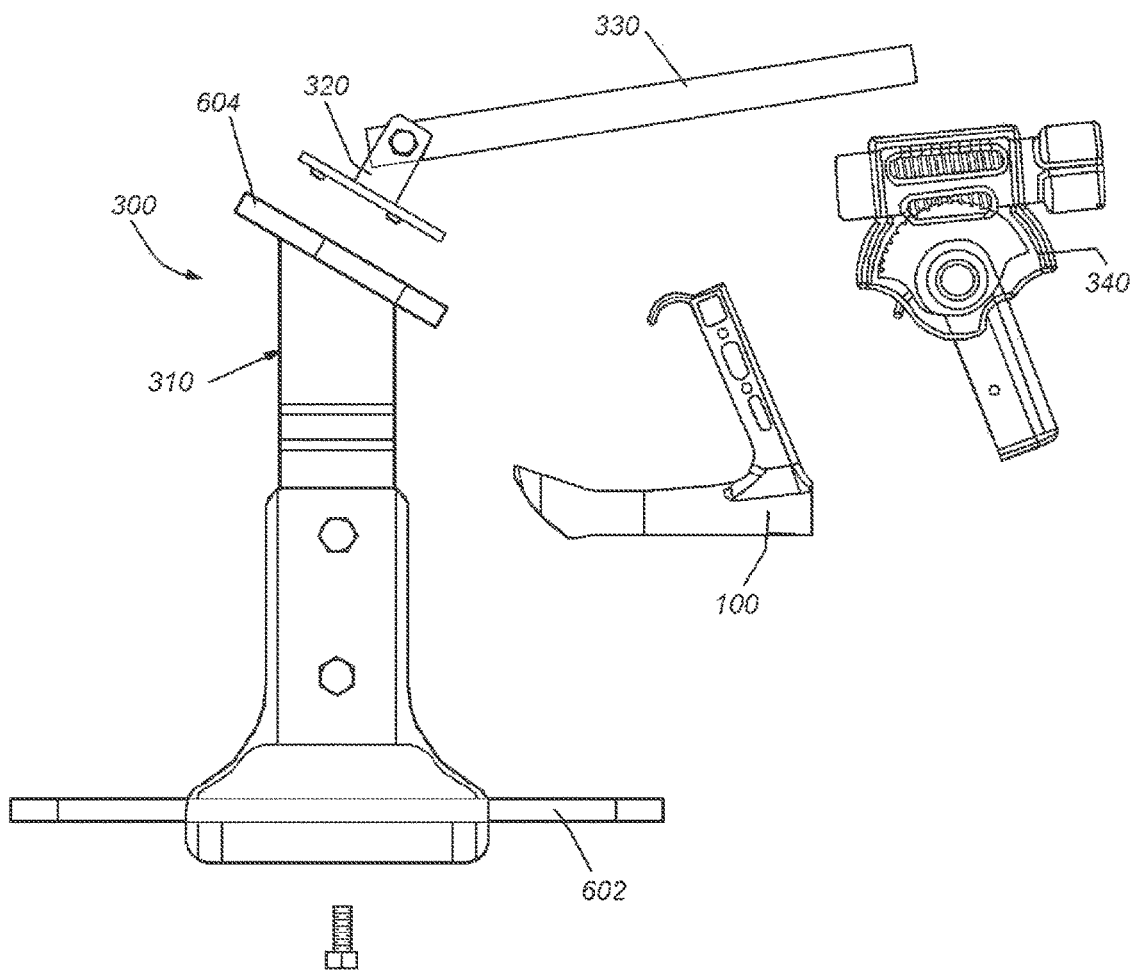
FIG. 7B is an exploded side view of a support rig and a laryngoscope, according to the embodiment.
Figure 7C:
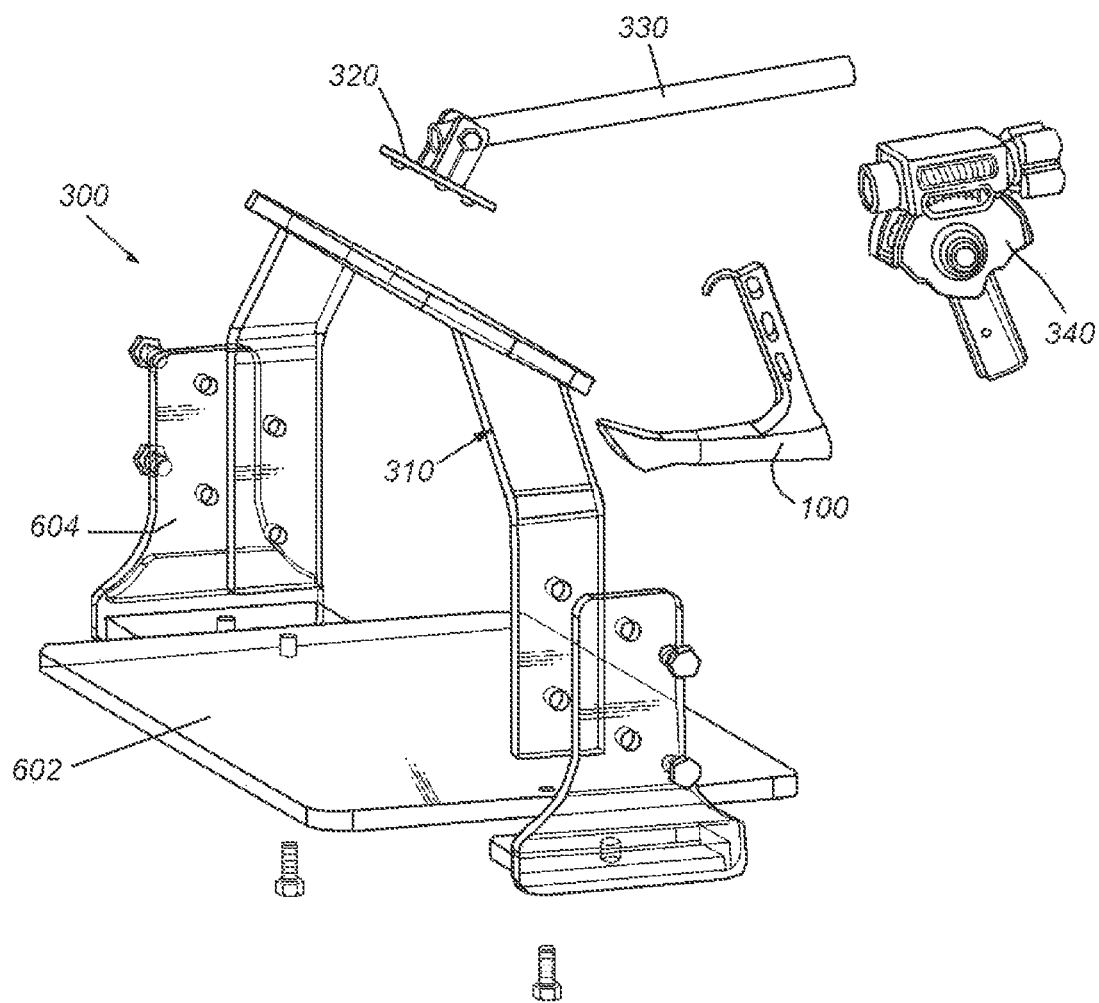
FIG. 7C is an exploded perspective view of a support rig and a laryngoscope from an alternate perspective, according to the embodiment.

FIG. 7A is an exploded perspective view of a support rig and a laryngoscope, according to an embodiment, FIG. 7B is an exploded side view of the support rig and laryngoscope, according to the embodiment, and FIG. 7C is an exploded perspective view of the support rig and laryngoscope from an alternate perspective, according to the embodiment. Turning to FIGS. 7A-7C, a support rig 300 can have a frame 310, a wrist 320, an arm 330, and an elbow assembly 340. The frame 310 can have a platform 602 and a tower 604. Prior to a surgery, various components of the support rig can be separate from other components of the support rig. The laryngoscope 100 can be separate and the elbow assembly 340 can be separate. The arm 330, wrist 320, and at least a portion of the tower 604 can assembled together, and can be separate from other components. The platform 602 can be separate, or can be assembled with at least a portion of the tower 604. The platform 602 can be placed on a patient support surface, such an operating table or imaging table. A patient can be placed on the patient support surface and on the platform 602. The platform 602, tower 604, wrist 320, and arm 330 can be assembled together. The elbow assembly 340 can be engaged with the arm 330. The elbow assembly 340 can slide along the arm 330 into a desired position. The laryngoscope 100 can be inserted into the patient. The laryngoscope 100 can be engaged with the elbow assembly 340. In an alternate embodiment, a tower can be attached to the platform at one location, and the tower can be hinged so that all of the tower, or a portion of the tower, can be hinged out of the way while a patient is loaded onto the platform, and the tower can then be hinged back into place after the patient has been loaded onto the platform. In another alternate embodiment, the tower can swivel out of the way while the patient is loaded onto the platform, and can then be swiveled back into place and locked into place. In an embodiment, platform 602 can be omitted and tower 604 can attach to the patient bed directly.

Figure 8A:
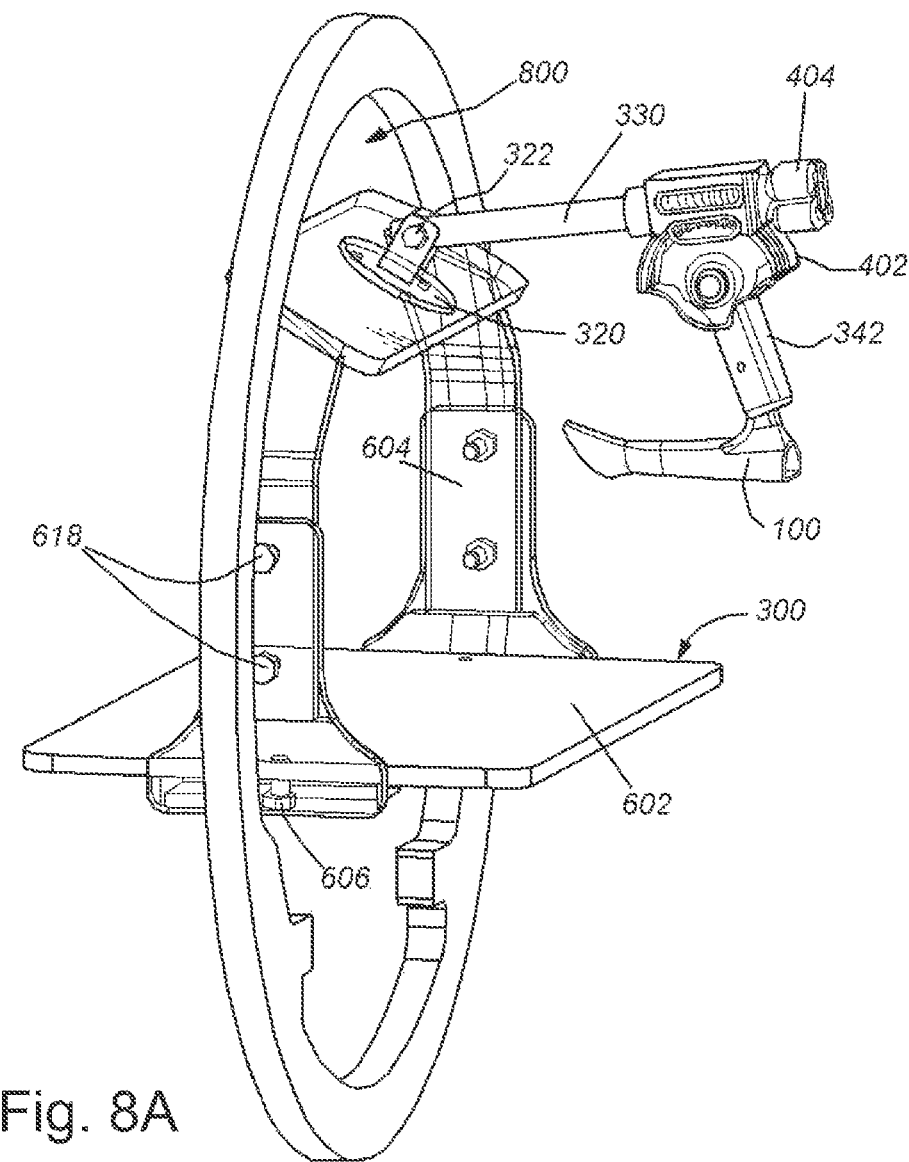
FIG. 8A is a perspective view of a support rig with an attached laryngoscope in the bore of a scanner, according to an embodiment.
Figure 8B:
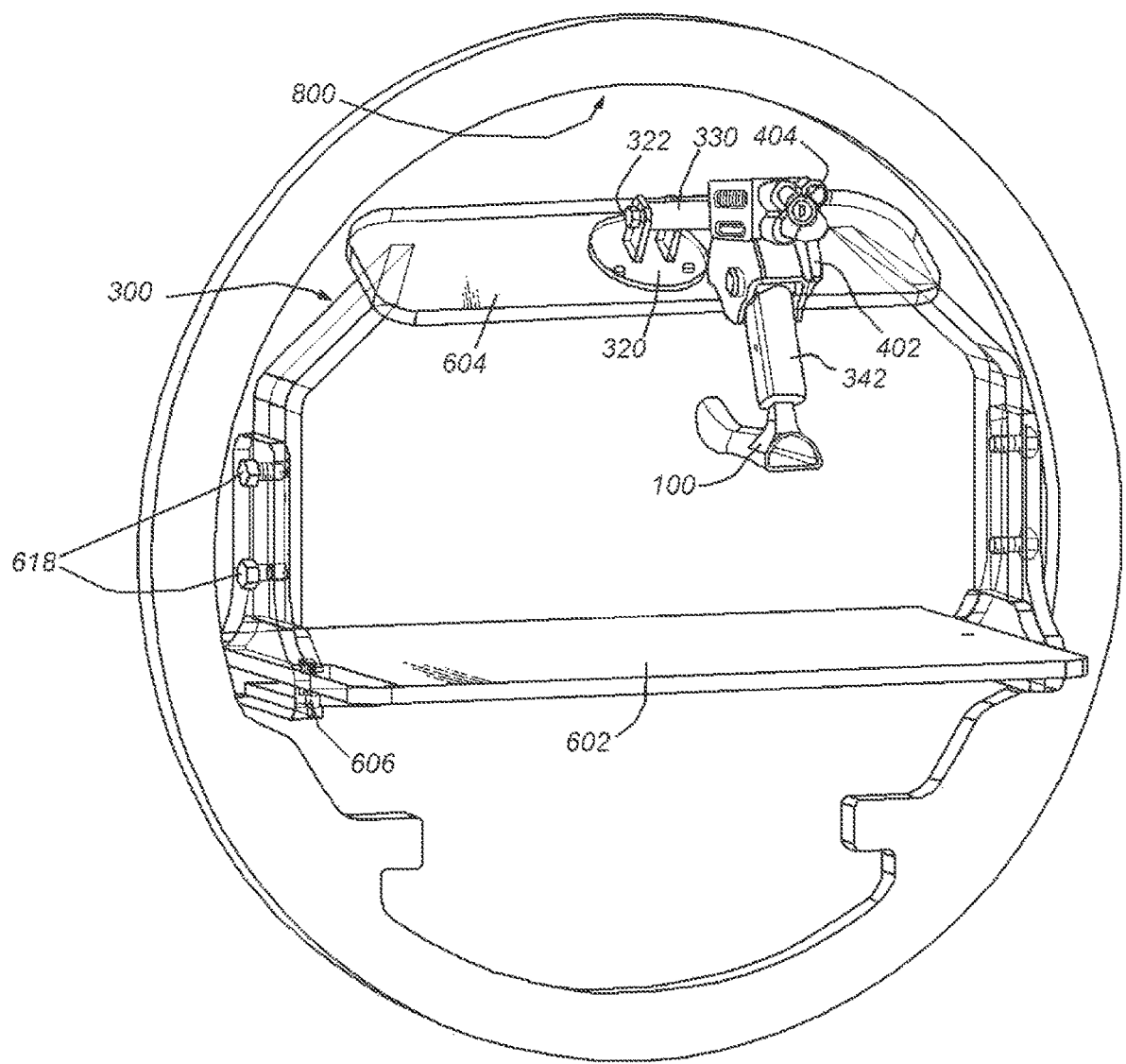
FIG. 8B is a perspective view of a support rig with an attached laryngoscope in the bore of a scanner from an alternate perspective, according to the embodiment.

FIG. 8A is a perspective view of a support rig with an attached laryngoscope in the bore of a scanner, according to an embodiment, and FIG. 8B is a perspective view of the support rig with the attached laryngoscope in the bore of a scanner from an alternate perspective, according to the embodiment. Turning to FIGS. 8A and 8B, an imager opening 800 is shown. The imager opening 800 can be the opening to an MRI scanner, a CT scanner, or other imaging equipment. The support rig 300 is adapted for use within various imaging devices, such as MRI scanners and CT scanners. The support rig 300 is free of metal components. The platform 602 can be made of a polymer such as poly(methyl methacrylate) (acrylic), or can be polyethylene, polycarbonate, polyamide (nylon) and/or polyvinyl chloride. The tower 604 can be made of a polymer such as poly (methyl methacrylate) (acrylic), or can be polyethylene, polycarbonate, polyamide (nylon) and/or polyvinyl chloride. The at least one tower bolt 606 and at least one leg bolt 618 can be made of a polymer such as poly(methyl methacrylate) (acrylic), or can be polyethylene, polycarbonate, polyamide (nylon), and/or polyvinyl chloride. The wrist 320 can be made of a polymer such as poly(methyl methacrylate) (acrylic), or can be polyethylene, polycarbonate, polyamide (nylon) and/or polyvinyl chloride. The hinge 322 can be made of a polymer such as poly(methyl methacrylate) (acrylic), or can be polyethylene, polycarbonate, polyamide (nylon), and/or polyvinyl chloride. The arm 330 can be made of a polymer such as poly(methyl methacrylate) (acrylic), or can be polyethylene, polycarbonate, polyamide (nylon), and/or polyvinyl chloride. The adjuster 404 and holder 342 can be made of a polymer such as poly(methyl methacrylate) (acrylic), or can be polyethylene, polycarbonate, polyamide (nylon), and/or polyvinyl chloride. The outer shell 402 can be made of a polymer such as poly(methyl methacrylate) (acrylic), or can be polyethylene, polycarbonate, polyamide (nylon), and/or polyvinyl chloride. The laryngoscope 100, that can be made of a polymer such as poly(methyl methacrylate) (acrylic), or can be polyethylene, polycarbonate, polyamide (nylon) and/or polyvinyl chloride, is adapted for use in imaging devices. The support rig 300, with an attached laryngoscope 100, can shaped and sized to be adapted for use within the bore of an imaging device. Because the support rig 300 and laryngoscope 100 are made of non-metallic materials, and because they are shaped and sized to fit within the bore of an imaging device, a patient with an inserted laryngoscope 100 can be inserted into an imaging device and an image can be taken of the patient with the inserted laryngoscope 100 that is supported by the rig 300.

A user can obtain an image of anatomical structures of a patient while the laryngoscope 100 is inserted in the throat, and while the laryngoscope is supported by the rig 300, so that the images obtained by the user will accurately show the locations of tumors or other anatomical structures while the user's head is tilted back and the laryngoscope is inserted. The rig 300 can maintain the position and orientation of the laryngoscope 100 while the patient is inserted into an imaging device, an image is taken, the patient is removed from the imaging device, and/or surgery is performed on the patient. The rig enables the user to rely on the images as being accurate while surgery is performed, because the position and orientation of the laryngoscope relative to the patient does not change after the user fixes the position and orientation of the laryngoscope relative to the patient, unless the user readjusts the position and orientation of the laryngoscope. A user can fix the position and orientation of the laryngoscope 100, then take an image of the patient with the laryngoscope 100 inserted, and can then adjust the position and orientation of the laryngoscope 100, if necessary, based on the information obtained in the image taken with the inserted laryngoscope 100. The process of adjusting the position and/or orientation of the laryngoscope 100, then taking an image, and then readjusting the position and/or orientation or the laryngoscope 100 can be repeated as necessary until the laryngoscope has been adjusted into the desired position and orientation.

It should be clear that a rig 300 is not limited to holding laryngoscopes, and a rig can be used to support a variety of medical instruments, including other retractors, that can be used during surgery, including laparoscopy instruments or others. A variety of instruments for various surgeries can be inserted into a patient and can be supported in a rig. A rig can maintain the position and orientation of various instruments relative to a patient without being impacted by the breathing or other movements of a patient. A non-metallic rig can maintain the position and orientation of various non-metallic instruments relative to a patient while the patient is undergoing an imaging process.

Figure 9A:
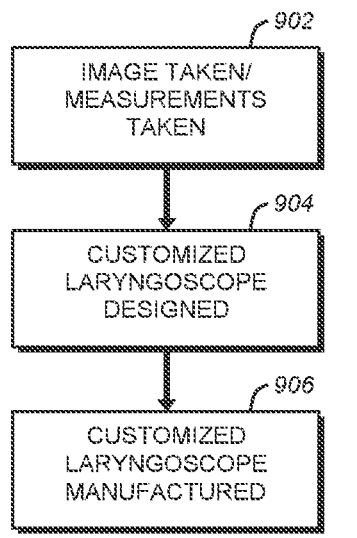
FIG. 9A is a flowchart showing the steps for making a customized laryngoscope, according to an embodiment.

FIG. 9A is a flowchart showing the steps for making a customized laryngoscope, according to an embodiment. At 902, an image can be taken of anatomical structures of a patient and/or the anatomical structures of the patient can be measured. At 904, a customized laryngoscope can be designed for use with the patient. The design of the laryngoscope can be based on multiple factors. The depth of the patient's throat can be a factor. The width of the patient's throat can be a factor. The location of an area of planned surgery can be a factor. The size and/or shape of a surgical tool to be used can be a factor. Other factors may be obvious to a person skilled in the art. A laryngoscope can be customized to the patient based on factors that the designer deems to be important for the application of the laryngoscope. At 906, a customized laryngoscope can be printed using a 3D printer of any acceptable type and operating modality or can be machined or injection molded using biocompatible materials. A customized laryngoscope can be printed thereby, using polymers such as MED610 from Stratasys.

Figure 9B:
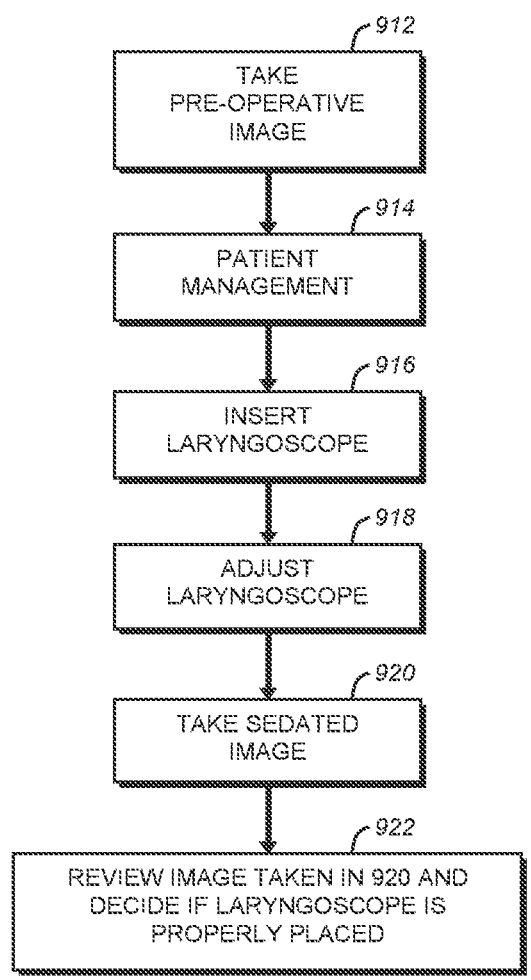
FIG. 9B is a flowchart describing the use of a laryngoscope and support rig to obtain images to inform a medical procedure, according to an embodiment.

FIG. 9B is a flowchart describing the use of a laryngoscope and support rig to obtain images to inform a surgery, according to an embodiment. At 912, a user, such as a doctor or hospital, can obtain at least one pre-operative image of anatomical structures of a patient. The images can be taken while the patient is awake or sedated, seated, lying down, or in another position, with or without the head tilted back, and with or without a laryngoscope inserted. The medical provider can use the obtained image to determine the locations of anatomical structures that may require surgery. 914 can include patient management. At 914, the patient can be sedated and/or placed on a platform 602 that is on a patient support surface such as in imaging table. At 916, the user can insert the laryngoscope 100, assemble the support rig 300 including the platform 602 that is under the patient, and attach the laryngoscope to the support rig. At 918, the user can adjust the position and/or orientation of the laryngoscope 100. The user can adjust the depth of the laryngoscope by moving the laryngoscope proximally and/or distally, in and/or out of the throat of the patient. The user can move the elbow assembly in a proximal and/or distal direction on the arm as the user adjusts the depth laryngoscope. The user can adjust the orientation of the laryngoscope by adjusting the angle between the arm 330 and the handle 110 of the laryngoscope 100. The user can place the laryngoscope in a position and orientation that the user estimates is optimal for the medical procedure, which can include viewing the anatomical structures and/or performing surgery. The user can fix the position and orientation of the laryngoscope relative to the patient. The user's estimate of an optimal position and orientation of the laryngoscope can be informed by an image taken before the laryngoscope is inserted. At 920, an image can be taken of the patient with the inserted laryngoscope 100 supported by the rig 300. The patient can be lying on an imaging table with a laryngoscope inserted and with the laryngoscope supported by a rig 300. An image can be taken of the anatomical structures of the patient with the laryngoscope inserted and supported by the rig. At 922, a user can review the image taken at 920, and can determine if the laryngoscope is correctly positioned and oriented, based on the actual location of a targeted anatomical structure, such as a tumor, relative to the laryngoscope. If the laryngoscope is correctly positioned and oriented relative to the target anatomical structure, the user and patient can proceed to surgery. If an adjustment to the position and/or orientation of the laryngoscope could put the laryngoscope into a better position and/or orientation for the medical procedure, the user can return to 918, and the user can repeat as necessary unto the laryngoscope is in the desired position and orientation relative to an anatomical structure of the patient.

Figure 9C:
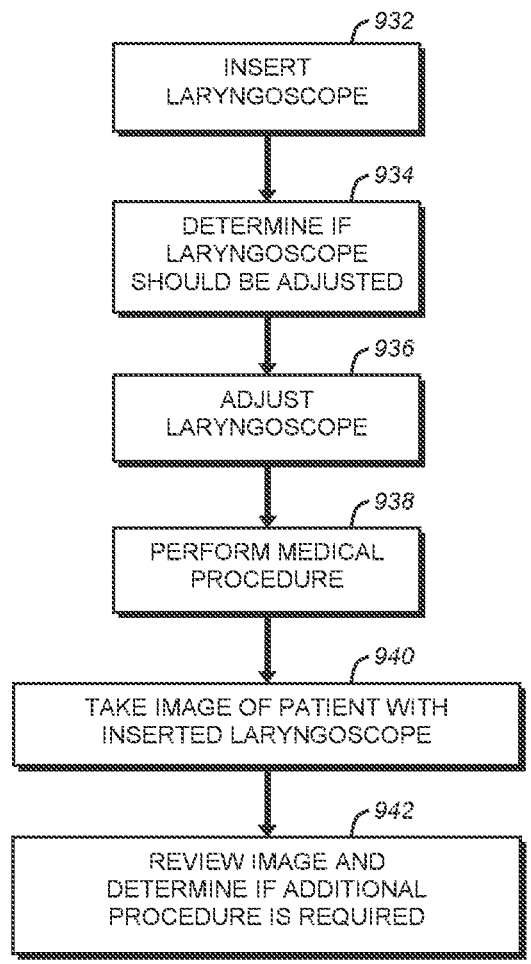
FIG. 9C is a flowchart describing the use of a laryngoscope and support rig during a medical procedure.

FIG. 9C is a flowchart describing the use of a laryngoscope and support rig during a medical procedure. At 932, the user can insert a laryngoscope 100, assemble the support rig 300 including the platform 602 that is under the patient, and attach the laryngoscope 100 to the support rig. At 934, the user can determine if the position and/or orientation of the laryngoscope should be adjusted. If the laryngoscope does not need adjusted, the user can proceed to step 936. If the laryngoscope should be adjusted, the user can proceed to step 936. At step 936, the user can adjust the position and/or orientation of the laryngoscope 100, if necessary. The user can adjust the depth of the laryngoscope by moving the laryngoscope proximally and/or distally, in and/or out of the throat of the patient. The user can move the elbow assembly in a proximal and/or distal direction on the arm as the user adjusts the depth laryngoscope. The user can adjust the orientation of the laryngoscope by adjusting the angle between the arm 330 and the handle 110 of the laryngoscope 100. The user can place the laryngoscope in a position and orientation that the user estimates is optimal for the medical procedure, which can include viewing the anatomical structures and/or performing surgery. The user can fix the position and orientation of the laryngoscope relative to the patient. The user's estimate of an optimal position and orientation of the laryngoscope can be informed by an image taken of the anatomical structures before the medical procedure is performed. At 938, the user can perform the medical procedure. This can include viewing the anatomical structures, and/or performing a surgery. Surgery can include laser surgery, including directing a laser down the throat of the patient towards a targeted anatomical structure that can include a tumor. The user can direct the laser through the central lumen 136 of the laryngoscope 100 towards the targeted anatomical structure. At 940, an image can be taken of the anatomical structures of the patient. The image is taken while the laryngoscope remains inserted into the patient and can be taken while the laryngoscope is supported by the rig and remains in a fixed position and orientation relative to the patient. At 942, the user can review the image taken at 940, and can determine if additional medical procedures are required, and what additional medical procedures are required. If the user determines that additional procedures are required, the user can return to step 934 and repeat as necessary.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments of the apparatus and method of the present invention, what has been described herein is merely illustrative of the application of the principles of the present invention. For example, different embodiments of wrists can incorporate different types of hinges, including hinges that enable movement of the arm through three dimensions, such as a ball-and-socket type joint, or other hinges that enable movement in multiple directions. A laryngoscope and an elbow assembly can be designed to snap together or use other engagement means that can be free of bolts or pins. Additionally, while a pair of clamps are shown, a unitary or integral clamping assembly that is bolted to the collar (e.g. at the front and rear as shown herein) can be employed in alternate embodiments. Also, as used herein, various directional and orientational terms (and grammatical variations thereof) such as "vertical", "horizontal", "up", "down", "bottom", "top", "side", "front", "rear", "left", "right", "forward", "rearward", and the like, are used only as relative conventions and not as absolute orientations with respect to a fixed coordinate system, such as the acting direction of gravity. Additionally, where the term "substantially" or "approximately" is employed with respect to a given measurement, value or characteristic, it refers to a quantity that is within a normal operating range to achieve desired results, but that includes some variability due to inherent inaccuracy and error within the allowed tolerances (e.g. 1-2%) of the system. Accordingly, this description is meant to be taken only by way of example, and not to otherwise limit the scope of this invention.

What is claimed is:

1. A positioning device for a medical instrument comprising:
    an adjuster comprising a worm gear;
    an axle;
    a medical instrument holder comprising,
        an engagement arm adapted to hold a medical instrument;
        an upper arc that is a segment of a cylinder, wherein a central axis of the cylinder passes through a center of the axle; and
    a rack gear, wherein the rack gear is arranged on the upper arc; and
    an outer shell, wherein the axle is engaged with the outer shell, and wherein the outer shell holds the worm gear and the rack in engagement, whereby the medical instrument holder pivots around the central axis when the worm gear is turned.

2. The positioning device of claim 1, the positioning device further comprising a bore through the positioning device from a distal end to a proximal end.

3. The positioning device of claim 2, wherein the bore is through the adjuster.

4. The positioning device of claim 1, wherein the positioning device is made of at least one non-metallic material.

5. The positioning device of claim 4, wherein the at least one non-metallic material is selected from the group consisting of poly(methyl methacrylate) (acrylic), polyethylene, polycarbonate, polyamide (nylon) and polyvinyl chloride.

6. The positioning device of claim 5, wherein the engagement arm defines a channel adapted to receive a medical instrument.

7. A support apparatus for a medical instrument comprising:
   a tower;
   an arm hingedly mounted to the tower; and
   a positioning device for a medical instrument, the positioning device adapted to be engaged with the arm, and the positioning device comprising;
      an adjuster comprising a worm gear;
      an axle;
      a medical instrument holder comprising:
         an engagement arm adapted to hold a medical instrument;
         an upper arc that is a segment of a cylinder, wherein a central axis of the cylinder passes through a center of the axle; and
         a rack gear, wherein the rack gear is arranged on the upper arc; and
      an outer shell, wherein the axle is engaged with the outer shell, and
   wherein the outer shell holds the worm gear and the rack in engagement, whereby the medical instrument holder pivots around the central axis when the worm gear is turned.

8. The support apparatus of claim 7, wherein the positioning device is selectively engageable with the arm.

9. The support apparatus of claim 7, wherein the positioning device is slidably engageable with the arm.

10. The support apparatus of claim 9, the positioning device further comprising a bore through the positioning device, the bore adapted to have the arm inserted into the bore.

11. The support apparatus of claim 7, wherein the support apparatus is made of at least one non-metallic material.

12. The support apparatus of claim 11, wherein the at least one non-metallic material is selected from the group consisting of poly(methyl methacrylate) (acrylic), polyethylene, polycarbonate, polyamide (nylon), and polyvinyl chloride.

13. The support apparatus of claim 7, further comprising a platform, wherein the tower extends upwardly from the platform.

14. The support apparatus of claim 13, wherein the tower is releasably engageable with the platform, so that the tower can be removed from the platform before a patient is placed on the platform, and the tower can be engaged with the platform after the patient is placed on the platform.

15. The support apparatus of claim 13, wherein the tower is hingedly engaged with the platform, so that the tower can be pivoted from a first position to a second position before a patient is placed on the platform, and the tower can pivoted from the second position to the first position after the patient is placed on the platform.

16. The support apparatus of claim 13, wherein the tower is swivellingly engaged with the platform, so that the tower can be swiveled from a first position to a second position before a patient is placed on the platform, and the tower can swiveled from the second position to the first position after the patient is placed on the platform.

* * * * *